(12) United States Patent
Rakos et al.

(10) Patent No.: US 7,560,006 B2
(45) Date of Patent: Jul. 14, 2009

(54) PRESSURE LAMINATION METHOD FOR FORMING COMPOSITE EPTFE/TEXTILE AND EPTFE/STENT/TEXTILE PROSTHESES

(75) Inventors: Ronald Rakos, Neshanic Station, NJ (US); Krzysztof Sowinski, Wallington, NJ (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 40 days.

(21) Appl. No.: 10/741,209

(22) Filed: Dec. 19, 2003

(65) Prior Publication Data

US 2004/0182511 A1 Sep. 23, 2004

Related U.S. Application Data

(63) Continuation-in-part of application No. 10/167,676, filed on Jun. 11, 2002, now abandoned, and a continuation-in-part of application No. 10/166,842, filed on Jun. 11, 2002.

(60) Provisional application No. 60/279,401, filed on Jun. 11, 2001.

(51) Int. Cl.
*B32B 37/00* (2006.01)
*B32B 37/10* (2006.01)
(52) U.S. Cl. .............. 156/293; 156/285; 156/287; 156/294; 156/295
(58) Field of Classification Search ............ 156/285, 156/293, 294, 295
See application file for complete search history.

(56) References Cited

U.S. PATENT DOCUMENTS 4,306,318 A 12/1981 Mano et al.
4,925,710 A 5/1990 Buck et al.

(Continued)

FOREIGN PATENT DOCUMENTS

EP 0 492 481 A1 7/1992

(Continued)

*Primary Examiner*—Justin Fischer
(74) *Attorney, Agent, or Firm*—Vidas, Arrett & Steinkraus, P.A.

(57) ABSTRACT

A method of forming a composite textile and ePTFE implantable device includes the steps of (a) providing an ePTFE layer having opposed surfaces comprising a microporous structure of nodes interconnected by fibrils; (b) providing a textile layer having opposed surfaces; (c) applying a coating of an elastomeric bonding agent to one of the opposed surfaces of the ePTFE layer or the textile layer; (d) providing a hollow member having an open end and an opposed closed end defining a fluid passageway therebetween and having a wall portion with at least one hole extending therethrough, the hole being in fluid communication with the fluid passageway; (e) concentrically placing the ePTFE layer and the textile layer onto the hollow member and over the at least one hole of the hollow member to provide an interior composite layer and an exterior composite layer, thereby defining a composite assembly, wherein the interior composite layer is one of the ePTFE layer or the textile layer and the exterior composite layer is the other of the ePTFE layer or the textile layer; (f) placing the hollow member with the composite assembly within a pressure chamber; (g) applying a pressure differential so that the pressure within the chamber is greater than a pressure within the fluid passageway of the hollow member; and (h) applying heat to the bonding agent to adhesively bond the textile layer and the ePTFE layer to provide a laminated composite assembly.

33 Claims, 19 Drawing Sheets

U.S. PATENT DOCUMENTS

| | | |
|---|---|---|
| 4,955,899 A | 9/1990 | Della Corna et al. |
| 5,026,591 A | 6/1991 | Henn et al. |
| 5,100,422 A | 3/1992 | Berguer et al. |
| 5,104,400 A | 4/1992 | Berguer et al. |
| 5,123,917 A | 6/1992 | Lee |
| 5,133,742 A | 7/1992 | Pinchuk |
| 5,152,782 A | 10/1992 | Kowligi et al. |
| 5,229,431 A | 7/1993 | Pinchuk |
| 5,282,824 A | 2/1994 | Gianturco |
| 5,387,236 A | 2/1995 | Noishiki et al. |
| 5,389,106 A | 2/1995 | Tower |
| 5,462,704 A | 10/1995 | Chen et al. |
| 5,466,509 A | 11/1995 | Kowligi et al. |
| 5,507,771 A | 4/1996 | Gianturco |
| 5,527,353 A * | 6/1996 | Schmitt .................... 623/1.44 |
| 5,562,697 A | 10/1996 | Christiansen |
| 5,562,728 A | 10/1996 | Lazarus et al. |
| 5,591,195 A | 1/1997 | Taheri et al. |
| 5,620,763 A | 4/1997 | House et al. |
| 5,628,788 A | 5/1997 | Pinchuk |
| 5,653,697 A | 8/1997 | Quiachon et al. |
| 5,674,241 A | 10/1997 | Bley et al. |
| 5,693,085 A | 12/1997 | Buirge et al. |
| 5,700,285 A | 12/1997 | Myers et al. |
| 5,713,917 A | 2/1998 | Leonhardt et al. |
| 5,718,973 A | 2/1998 | Lewis et al. |
| 5,735,892 A | 4/1998 | Myers et al. |
| 5,749,880 A | 5/1998 | Banas et al. |
| 5,799,384 A | 9/1998 | Schwartz et al. |
| 5,800,510 A | 9/1998 | Schmitt |
| 5,800,512 A | 9/1998 | Lentz et al. |
| 5,810,870 A | 9/1998 | Myer et al. |
| 5,824,042 A | 10/1998 | Lombardi et al. |
| 5,824,053 A | 10/1998 | Khosravi et al. |
| 5,824,054 A | 10/1998 | Khosravi et al. |
| 5,836,926 A | 11/1998 | Peterson et al. |
| 5,843,158 A | 12/1998 | Lenker et al. |
| 5,843,161 A | 12/1998 | Solovay |
| 5,843,166 A | 12/1998 | Lentz et al. |
| 5,916,264 A | 6/1999 | Von Oepen et al. |
| 5,922,443 A * | 7/1999 | Larsen et al. ................ 428/217 |
| 5,925,074 A | 7/1999 | Gingras et al. |
| 5,925,075 A | 7/1999 | Myers et al. |
| 5,928,279 A | 7/1999 | Shannon et al. |
| 5,957,974 A | 9/1999 | Thompson et al. |
| 5,961,545 A * | 10/1999 | Lentz et al. ................ 623/1.39 |
| 5,961,546 A | 10/1999 | Robinson et al. |
| 5,976,192 A | 11/1999 | McIntyre et al. |
| 6,001,056 A | 12/1999 | Jassawalla et al. |
| 6,001,125 A | 12/1999 | Golds et al. |
| 6,005,191 A * | 12/1999 | Tzeng et al. ............ 174/102 R |
| 6,019,778 A | 2/2000 | Wilson et al. |
| 6,036,724 A | 3/2000 | Lentz et al. |
| 6,042,578 A | 3/2000 | Dinh et al. |
| 6,070,973 A * | 6/2000 | Sachs et al. .................... 347/75 |
| 6,075,180 A | 6/2000 | Sharber et al. |
| 6,080,198 A | 6/2000 | Lentz et al. |
| 6,099,557 A | 8/2000 | Schmitt |
| 6,120,539 A | 9/2000 | Eldridge et al. |
| 6,124,523 A | 9/2000 | Banas et al. |
| 6,136,022 A | 10/2000 | Nunez et al. |
| 6,139,573 A | 10/2000 | Sogard et al. |
| 6,159,239 A | 12/2000 | Greenhalgh |
| 6,187,054 B1 | 2/2001 | Colone et al. |
| 6,203,735 B1 | 3/2001 | Edwin et al. |
| 6,214,039 B1 * | 4/2001 | Banas et al. ................ 623/1.13 |
| 6,309,343 B1 | 10/2001 | Lentz et al. |
| 6,331,191 B1 | 12/2001 | Chobotov |
| 6,344,052 B1 | 2/2002 | Greenan et al. |
| 6,375,787 B1 | 4/2002 | Lukic |
| 6,391,052 B2 | 5/2002 | Buirge et al. |
| 6,428,571 B1 * | 8/2002 | Lentz et al. ................. 623/1.4 |
| 6,443,981 B1 | 9/2002 | Colone et al. |
| 6,540,773 B2 | 4/2003 | Dong |
| 6,540,780 B1 | 4/2003 | Zilla et al. |
| 6,554,855 B1 | 4/2003 | Dong |
| 6,626,939 B1 * | 9/2003 | Burnside et al. ............ 623/1.38 |
| 6,797,311 B2 * | 9/2004 | Loomis et al. ............. 427/2.24 |
| 6,808,533 B1 * | 10/2004 | Goodwin et al. .......... 623/1.13 |
| 6,981,870 B2 * | 1/2006 | Heasley .................... 433/139 |
| 7,108,716 B2 * | 9/2006 | Burnside et al. ............ 623/1.38 |
| 2003/0060871 A1 | 3/2003 | Hill et al. |
| 2003/0116260 A1 | 6/2003 | Chobotov et al. |
| 2003/0204241 A1 | 10/2003 | Dong |

FOREIGN PATENT DOCUMENTS

| | | | |
|---|---|---|---|
| EP | 0775472 A2 | | 5/1997 |
| EP | 855170 | * | 7/1998 |
| EP | 0775472 A3 | | 4/2000 |
| GB | 1227554 | * | 4/1971 |
| JP | 59199235 | * | 11/1984 |
| JP | 59218832 | * | 12/1984 |
| JP | 03203613 | * | 9/1991 |
| WO | WO 87/05796 | | 10/1987 |
| WO | WO 96/35577 | | 11/1996 |
| WO | WO 00/47271 | | 8/2000 |
| WO | WO 01/32382 | | 5/2001 |
| WO | WO 02/43621 | | 6/2002 |
| WO | WO 02/100454 | | 12/2002 |
| WO | WO 03/103736 | | 12/2003 |

* cited by examiner

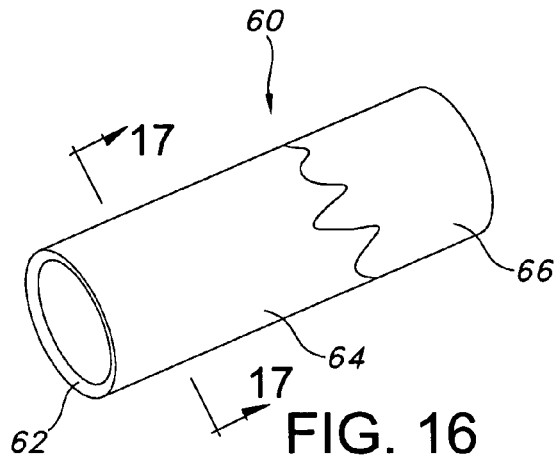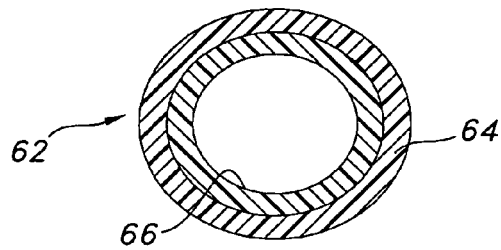
FIG. 16
FIG. 17
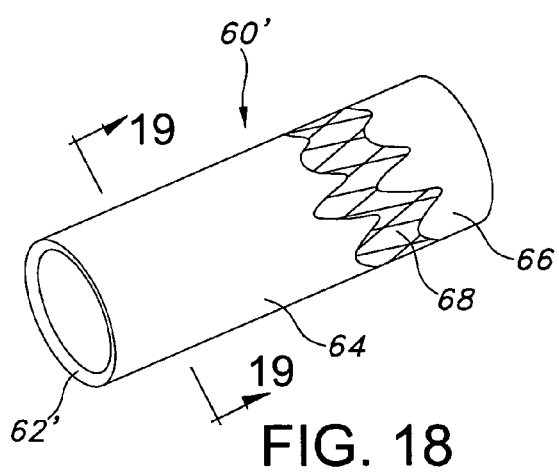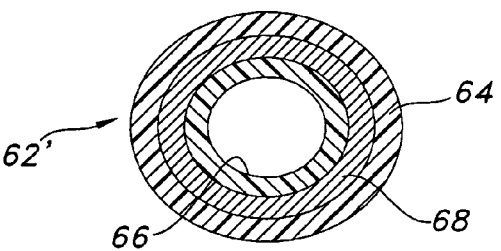
FIG. 18
FIG. 19
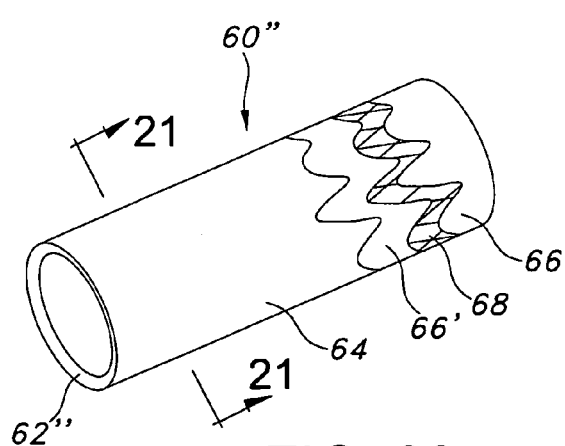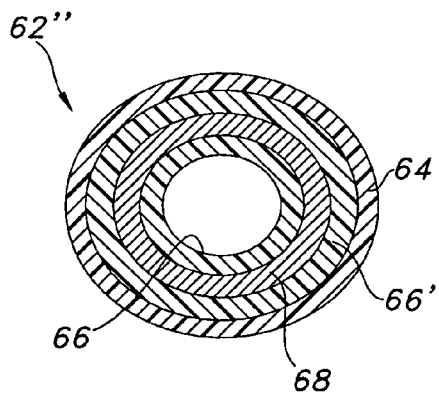
FIG. 20
FIG. 21

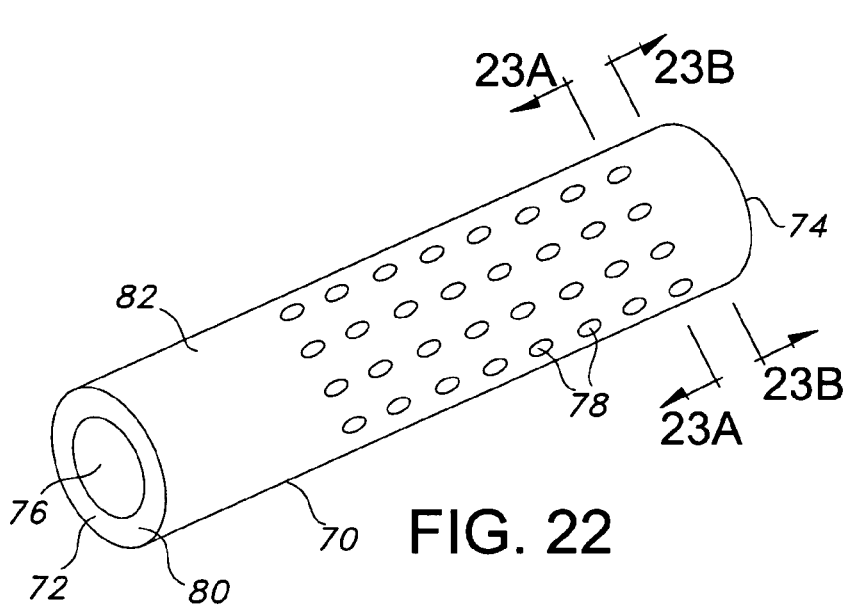
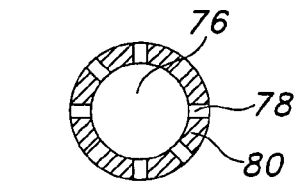
FIG. 22
FIG. 23A
FIG. 23B
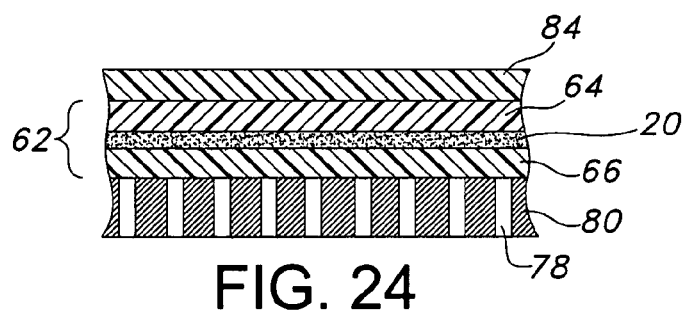
FIG. 24
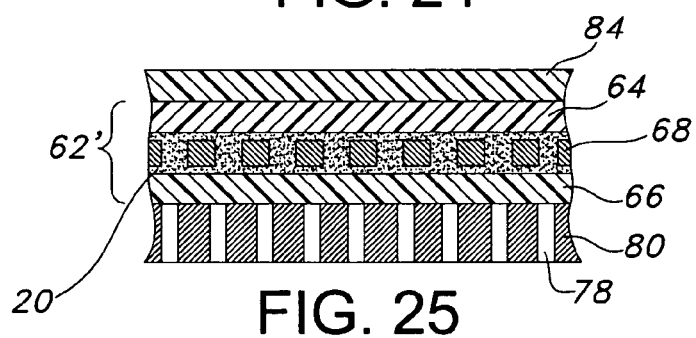
FIG. 25
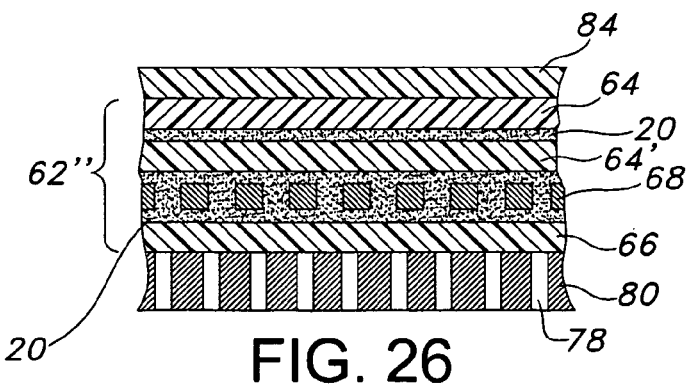
FIG. 26

PRESSURE LAMINATION METHOD FOR FORMING COMPOSITE EPTFE/TEXTILE AND EPTFE/STENT/TEXTILE PROSTHESES

CROSS-REFERENCE TO RELATED APPLICATIONS

This application is a continuation-in-part of application Ser. No. 10/167,676, filed Jun. 11, 2002, now abandoned which claims the benefit of Provisional Application No. 60/279,401, filed Jun. 11, 2001, and is also a continuation-in-part of application Ser. No. 10/166,842, filed Jun. 11, 2002, the contents all of which are incorporated herein by reference.

FIELD OF THE INVENTION

The present invention relates generally to an implantable prosthesis. More particularly, the present invention relates to a pressure lamination method for providing a composite multilayer implantable structure having a textile layer, an expanded polytetrafluoroethylene layer (ePTFE) and an elastomeric bonding agent layer or a heat or a pressure sensitive adhesive layer, preferably elastomeric, within the ePTFE porous layer, which joins the textile and ePTFE layer to form an integral structure.

BACKGROUND OF THE INVENTION

Implantable prostheses are commonly used in medical applications. One of the more common prosthetic structures is a tubular prosthesis which may be used as a vascular graft to replace or repair damaged or diseased blood vessel. To maximize the effectiveness of such a prosthesis, it should be designed with characteristics which closely resemble that of the natural body lumen which it is repairing or replacing.

One form of a conventional tubular prosthesis specifically used for vascular grafts includes a textile tubular structure formed by weaving, knitting, braiding or any non-woven textile technique processing synthetic fibers into a tubular configuration. Tubular textile structures have the advantage of being naturally porous which allows desired tissue ingrowth and assimilation into the body. This porosity, which allows for ingrowth of surrounding tissue, must be balanced with fluid tightness so as to minimize leakage during the initial implantation stage.

Attempts to control the porosity of the graft while providing a sufficient fluid barrier have focused on increasing the thickness of the textile structure, providing a tighter stitch construction and incorporating features such as velours to the graft structure. Further, most textile grafts require the application of a biodegradable natural coating, such as collagen or gelatin in order to render the graft blood tight. While grafts formed in this manner overcome certain disadvantages inherent in attempts to balance porosity and fluid tightness, these textile prostheses may exhibit certain undesirable characteristics. These characteristics may include an undesirable increase in the thickness of the tubular structure, which makes implantation more difficult. These textile tubes may also be subject to kinking, bending, twisting or collapsing during handling. Moreover, application of a coating may render the grafts less desirable to handle from a tactility point of view, and therefore more difficult to implant. Further such grafts may have a profile not suitable for use as an endovascular device.

It is also well known to form a prosthesis, especially a tubular graft, from polymers such as polytetrafluoroethylene (PTFE). A tubular graft may be formed by stretching and expanding PTFE into a structure referred to as expanded polytetrafluoroethylene (ePTFE). Tubes formed of ePTFE exhibit certain beneficial properties as compared with textile prostheses. The expanded PTFE tube has a unique structure defined by nodes interconnected by fibrils. The node and fibril structure defines micropores which facilitate a desired degree of tissue ingrowth while remaining substantially fluid-tight. Tubes of ePTFE may be formed to be exceptionally thin and yet exhibit the requisite strength necessary to serve in the repair or replacement of a body lumen. The thinness of the ePTFE tube facilitates ease of implantation and deployment with minimal adverse impact on the body.

While exhibiting certain superior attributes, ePTFE tubes are not without certain disadvantages. Grafts formed of ePTFE tend to be relatively non-compliant as compared with textile grafts and natural vessels. Further, while exhibiting a high degree of tensile strength, ePTFE grafts are susceptible to tearing. Additionally, ePTFE grafts lack the suture retention strength of coated textile grafts. This may cause undesirable bleeding at the suture hole. Thus, the ePTFE grafts lack many of the advantageous properties of certain textile grafts.

It is also known that it is extremely difficult to join PTFE and ePTFE to other materials via adhesives or bonding agents due to its chemically inert and non-wetting character. Wetting of the surface by the adhesive is necessary to achieve adhesive bonding. Thus, heretofore, attempts to bond ePTFE to other dissimilar materials, such as textiles, have been difficult.

It is also known to use vascular grafts in conjunction with support structures. Such support structures typically come in the form of stents, which are formed of metal or polymeric materials generally formed in a tubular structure and are used to hold a vein or artery open. Stents are well known in the art and may be self-expanding or radially expandable by balloon expansion. Examples of stent/graft configurations known in the art can be seen in U.S. Pat. Nos. 5,700,285; 5,749,880; and 5,123,917, each of which are herein incorporated by reference. It is advantageous to use stent/graft configurations because the stent provides and ensures the patency of the prosthesis, while the vascular graft provides biocompatible properties in a vessel more suitable for blood to flow through.

One method for laminating layers of ePTFE is disclosed in U.S. Pat. No. 6,139,573, the contents of which are incorporated herein by reference. The lamination process is described as using a heat-shrinkable sleeve and flowable mass particulate placed over a stent having inner and outer layers of ePTFE disposed thereover. Upon application of heat, the heat-shrinkable sleeve compresses the flowable mass articulate to provide a compressive force to permit adherence of the ePTFE layers through the openings of the stent. The use of such a heat-shrinkable sleeve and flowable mass particulate, however, complicated the lamination process. Further, the heat-shrinkable sleeve or tube is typically supplied in fixed ratios relative to the diameter of the stent, such as ratios of 4:1 or 2:1. This makes control of the amount of pressure applied, especially along the length of the stent and the ePTFE layers, difficult, leading to variability of the bonding strength along such lengths.

It is apparent that conventional textile prostheses as well as ePTFE prostheses have acknowledged advantages and disadvantages. Neither of the conventional prosthetic materials exhibits fully all of the benefits desirable for use as a vascular prosthesis.

It is therefore desirable to provide an implantable prosthesis, preferably in the form of a tubular vascular prosthesis, which achieves many of the above-stated benefits without the resultant disadvantages associated therewith. It is also desirable to provide an implantable multi-layered patch which also achieves the above-stated benefits without the disadvantages of similar conventional products.

The present invention provides a composite multi-layered implantable prosthetic structure which may be used in various applications, especially vascular applications. The implantable structure of the present invention may include an ePTFE-lined textile graft, an ePTFE graft, covered with a textile covering, or a vascular patch including a textile surface and an opposed ePTFE surface. Moreover, additional ePTFE and/or textile layers may be combined with any of these embodiments.

The composite multi-layered implantable structure of the present invention includes a first layer formed of a textile material and a second layer formed of expanded polytetrafluoroethylene (ePTFE) having a porous microstructure defined by nodes interconnected by fibrils. An elastomeric bonding agent is applied to either the first or the second layer and disposed within the pores of the microstructure for securing the first layer to the second layer.

The bonding agent may be selected from a group of materials including biocompatible elastomeric materials such as urethanes, silicones, isobutylene/styrene copolymers, block polymers and combinations thereof.

The tubular composite grafts of the present invention may also be formed from appropriately layered sheets which can then be overlapped to form tubular structures. Bifurcated, tapered conical and stepped-diameter tubular structures may also be formed from the present invention.

The first layer may be formed of various textile structures including knits, weaves, stretch knits, braids, any non-woven textile processing techniques, and combinations thereof. Various biocompatible polymeric materials may be used to form the textile structures, including polyethylene terephthalate (PET), naphthalene dicarboxylate derivatives such as polyethylene naphthalate, polybutylene naphthalate, polytrimethylene naphthalate, trimethylenediol naphthalate, ePTFE, natural silk, polyethylene and polypropylene, among others. PET is a particularly desirable material for forming the textile layer.

The bonding agent may be applied in a number of different forms to either the first or the second layer. Preferably, the bonding agent is applied in solution to one surface of the ePTFE layer, preferably by spray coating. The textile layer is then placed in contact with the coated surface of the ePTFE layer. The bonding agent may also alternatively be in the form of a solid tubular structure. The bonding agent may also be applied in powder form, and may also be applied and activated by thermal and/or chemical processing well known in the art.

The present invention more specifically provides an ePTFE-lined textile graft. The lined textile graft includes a tubular textile substrate bonded using a biocompatible elastomeric material to a tubular liner of ePTFE. A coating of an elastomeric bonding agent may be applied to the surface of the ePTFE liner so that the bonding agent is present in the micropores thereof. The coated liner is then secured to the tubular textile structure via the elastomeric binding agent. The liner and textile graft can each be made very thin and still maintain the advantages of both types of materials.

The present invention further provides a textile-covered ePTFE graft. The tubular ePTFE graft structure includes micropores defined by nodes interconnected by fibrils. A coating of an elastomeric bonding agent is applied to the surface of the ePTFE tubular structure with the bonding agent being resident within the microporous structure thereof. A tubular textile structure is applied to the coated surface of the ePTFE tubular structure and secured thereto by the elastomeric bonding agent.

Additionally, the present invention provides an implantable patch which may be used to cover an incision made in a blood vessel, or otherwise support or repair a soft tissue body part, such as a vascular wall. The patch of the present invention includes an elongate ePTFE substrate being positioned as the interior surface of a vascular wall. The opposed surface is coated with a bonding agent, such that the bonding agent resides within the microporous structure of the ePTFE substrate. A planar textile substrate is positioned over the coated surface of the ePTFE substrate so as to form a composite multi-layered implantable structure.

The composite multi-layered implantable structures of the present invention are designed to take advantage of the inherent beneficial properties of the materials forming each of the layers. The textile layer provides for enhanced tissue ingrowth, high suture retention strength and longitudinal compliance for ease of implantation. The ePTFE layer provides the beneficial properties of sealing the textile layer without need for coating the textile layer with a sealant such as collagen. The sealing properties of the ePTFE layer allow the wall thickness of the textile layer to be minimized. Further, the ePTFE layer exhibits enhanced thrombo-resistance upon implantation. Moreover, the elastomeric bonding agent not only provides for an integral composite structure, but also may add further puncture-sealing characteristics to the final prosthesis.

In further aspects of the invention, the implantable structure may be used in conjunction with radially-expandable members such as stents and other structures which are capable of maintaining patency of the implantable structure in a bodily vessel. For example, a stent may be disposed over a layer of ePTFE with the stent and the layer of ePTFE being joined to the textile tubular structure via the elastomeric bonding agent or a stent may be disposed between two ePTFE layers with the outer ePTFE layer being joined to the tubular textile structure via the elastomeric bonding agent. Any stent construction known to those skilled in the art may be used, including self-expanding stents, as well as, balloon-expandable stents.

A method of forming a composite textile and ePTFE implantable device includes the steps of (a) providing an ePTFE layer having opposed surfaces comprising a microporous structure of nodes interconnected by fibrils; (b) providing a textile layer having opposed surfaces; (c) applying a coating of an elastomeric bonding agent to one of the opposed surfaces of the ePTFE layer or the textile layer; (d) providing a hollow member having an open end and an opposed closed end defining a fluid passageway therebetween and having a wall portion with at least one hole extending therethrough, the hole being in fluid communication with the fluid passageway; (e) concentrically placing the ePTFE layer and the textile layer onto the hollow member and over the at least one hole of the hollow member to provide an interior composite layer and an exterior composite layer, thereby defining a composite assembly, wherein the interior composite layer is one of the ePTFE layer or the textile layer and the exterior composite layer is the other of the ePTFE layer or the textile layer; (f) placing the hollow member with the composite assembly within a pressure chamber; (g) applying a pressure differential so that the pressure within the chamber is greater than a pressure within the fluid passageway of the hollow member; and (h) applying heat to the bonding agent to adhesively bond the textile layer and the ePTFE layer to provide a laminated composite assembly.

Further, a silicone layer may be applied or placed over the textile/adhesive/ePTFE composite prior to placement in the pressure chamber. The silicone layer acts as a transfer layer through which the pressure differential is applied and does not act by itself as a force-supplying material as with the heat-shrinkable methods of the prior art.

In one aspect of the present invention, a composite vascular prosthesis formed by the methods of the present invention has a bond shear strength of at least 5.5 g/mm$^2$ and a variation of said bond shear strength of less than about 2. In another aspect of the present invention, a composite vascular prosthesis formed by the methods of the present invention has a bond peel strength of at least 32 g/mm and a variation of said bond peel strength of less than about 4.

Various additives such as drugs, growth-factors, anti-microbial, anti-thrombogenic agents and the like may also be employed.

BRIEF DESCRIPTION OF THE DRAWINGS

FIGS. 16-21 show a partial cut-away perspective view of prostheses of the present invention and corresponding cross-sectional views thereof.

FIGS. 22 through 23B show a hollow mandrel useful for pressure lamination of tubular prostheses of the present invention.

FIGS. 24-26 show a partial cross-sectional view of the prostheses of FIGS. 16-21 on the hollow mandrel of FIGS. 22-23.

DETAILED DESCRIPTION OF THE PREFERRED EMBODIMENT:

The present invention provides a composite implantable prosthesis, desirably a vascular prosthesis including a layer of ePTFE and a layer of a textile material which are secured together by an elastomeric bonding agent. The vascular prosthesis of the present invention may include a ePTFE-lined textile vascular graft, an ePTFE vascular graft including a textile covering and a composite ePTFE/textile vascular patch.

Figure 1:
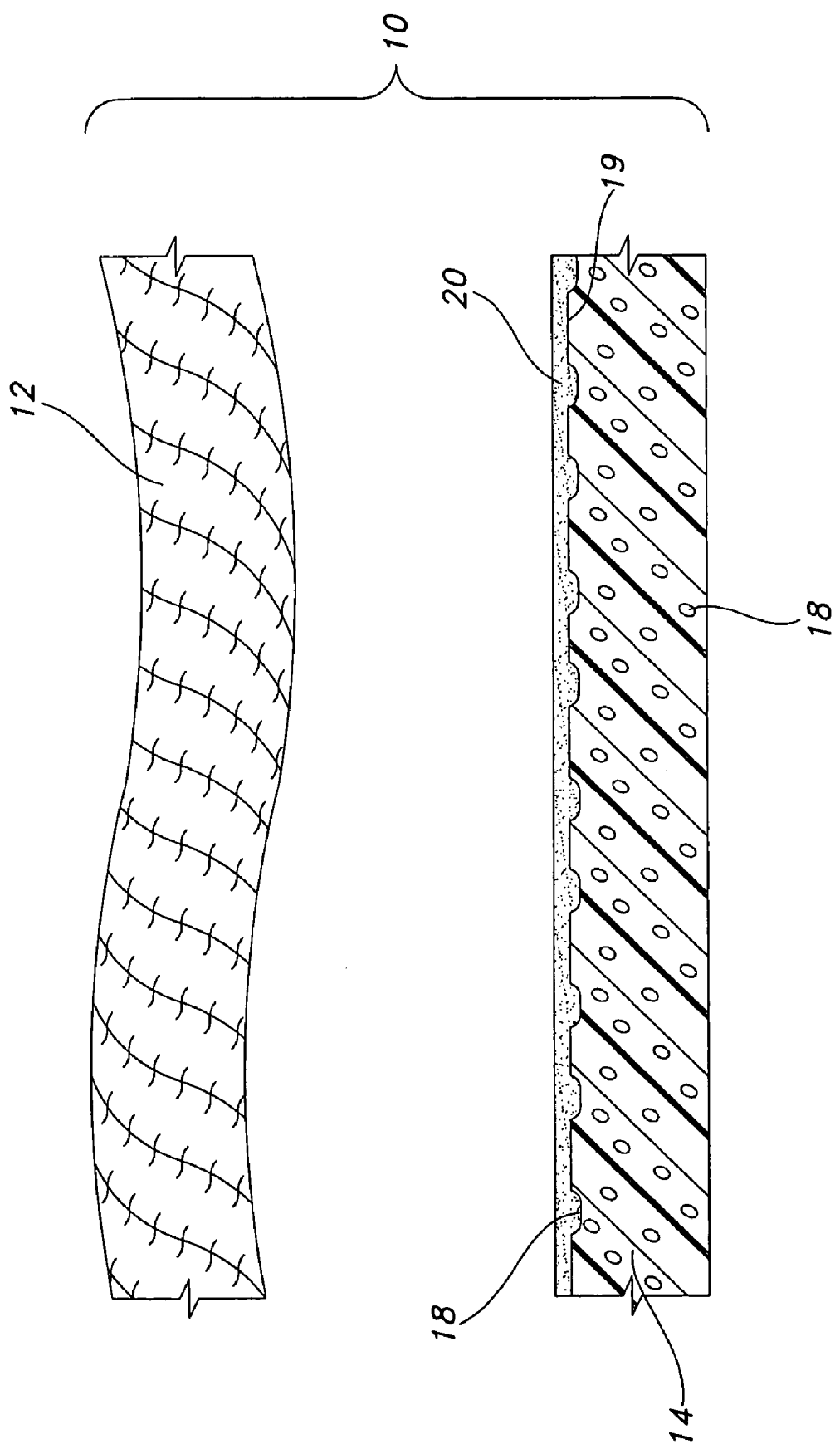
FIG. 1 shows a schematic cross-section, a portion of a composite multi-layered implantable structure of the present invention.

Referring to FIG. 1, a schematic cross-section of a portion of a representative vascular prosthesis 10 is shown. As noted above, the prosthesis 10 may be a portion of a graft, patch or any other implantable structure.

The prosthesis 10 includes a first layer 12 which is formed of a textile material. The textile material 12 of the present invention may be formed from synthetic yarns that may be flat, shaped, twisted, textured, pre-shrunk or un-shrunk. Preferably, the yarns are made from thermoplastic materials including, but not limited to, polyesters, polypropylenes, polyethylenes, polyurethanes, polynaphthalenes, polytetrafluoroethylenes and the like. The yarns may be of the multifilament, monofilament or spun types. In most vascular applications, multifilaments are preferred due to the increase in flexibility. Where enhanced crush resistance is desired, the use of monofilaments have been found to be effective. As is well known, the type and denier of the yarn chosen are selected in a manner which forms a pliable soft tissue prosthesis and, more particularly, a vascular structure have desirable properties.

The prosthesis 10 further includes a second layer 14 formed of expanded polytetrafluoroethylene (ePTFE). The ePTFE layer 14 may be produced from the expansion of PTFE formed in a paste extrusion process. The PTFE extrusion may be expanded and sintered in a manner well known in the art to form ePTFE having a microporous structure defined by nodes interconnected by elongate fibrils. The distance between the nodes, referred to as the internodal distance (IND), may be varied by the parameters employed during the expansion and sintering process. The resulting process of expansion and sintering yields pores 18 within the structure of the ePTFE layer. The size of the pores are defined by the IND of the ePTFE layer.

The composite prosthesis 10 of the present invention further includes a bonding agent 20 applied to one surface 19 of ePTFE layer 18. The bonding agent 20 is preferably applied in solution by a spray coating process. However, other processes may be employed to apply the bonding agent.

In the present invention, the bonding agent may include various biocompatible, elastomeric bonding agents such as urethanes, styrene/isobutylene/styrene block copolymers (SIBS), silicones, and combinations thereof. Other similar materials are contemplated. Most desirably, the bonding agent may include polycarbonate urethanes sold under the trade name CORETHANE®. This urethane is provided as an adhesive solution with preferably 7.5% Corethane, 2.5 W30, in dimethylacetamide (DMAc) solvent.

The term elastomeric as used herein refers to a substance having the characteristic that it tends to resume an original shape after any deformation thereto, such as stretching, expanding or compression. It also refers to a substance which has a non-rigid structure, or flexible characteristics in that it is not brittle, but rather has compliant characteristics contributing to its non-rigid nature.

The polycarbonate urethane polymers particularly useful in the present invention are more fully described in U.S. Pat. Nos. 5,133,742 and 5,229,431 which are incorporated in their entirety herein by reference. These polymers are particularly resistant to degradation in the body over time and exhibit exceptional resistance to cracking in vivo. These polymers are segmented polyurethanes which employ a combination of hard and soft segments to achieve their durability, biostability, flexibility and elastomeric properties.

The polycarbonate urethanes useful in the present invention are prepared from the reaction of an aliphatic or aromatic polycarbonate macroglycol and a diisocyanate n the presence of a chain extender. Aliphatic polycarbonate macroglycols such as polyhexane carbonate macroglycols and aromatic diisocyanates such as methylene diisocyanate are most desired due to the increased biostability, higher intramolecular bond strength, better heat stability and flex fatigue life, as compared to other materials.

The polycarbonate urethanes particularly useful in the present invention are the reaction products of a macroglycol, a diisocyanate and a chain extender.

A polycarbonate component is characterized by repeating

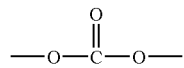

units, and a general formula for a polycarbonate macroglycol is as follows:

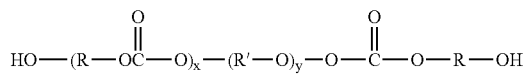

wherein x is from 2 to 35, y is 0, 1 or 2, R either is cycloaliphatic, aromatic or aliphatic having from about 4 to about 40 carbon atoms or is alkoxy having from about 2 to about 20 carbon atoms, and wherein R' has from about 2 to about 4 linear carbon atoms with or without additional pendant carbon groups.

Examples of typical aromatic polycarbonate macroglycols include those derived from phosgene and bisphenol A or by ester exchange between bisphenol A and diphenyl carbonate such as (4,4'-dihydroxy-diphenyl-2,2'-propane) shown below, wherein n is between about 1 and about 12.

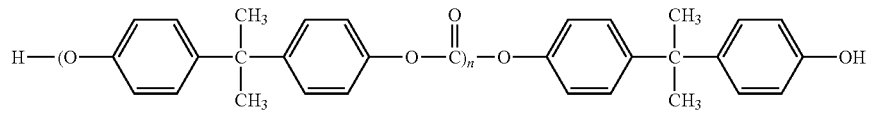

Typical aliphatic polycarbonates are formed by reacting cycloaliphatic or aliphatic diols with alkylene carbonates as shown by the general reaction below:

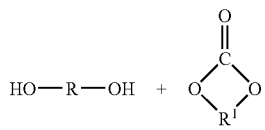

wherein R is cyclic or linear and has between about 1 and about 40 carbon atoms and wherein $R^1$ is linear and has between about 1 and about 4 carbon atoms.

Typical examples of aliphatic polycarbonate diols include the reaction products of 1,6-hexanediol with ethylene carbonate, 1,4-butanediol with propylene carbonate, 1,5-pentanediol with ethylene carbonate, cyclohexanedimethanol with ethylene carbonate and the like and mixtures of above such as diethyleneglycol and cyclohexanedimethanol with ethylene carbonate.

When desired, polycarbonates such as these can be copolymerized with components such as hindered polyesters, for example phthalic acid, in order to form carbonate/ester copolymer macroglycols. Copolymers formed in this manner can be entirely aliphatic, entirely aromatic, or mixed aliphatic and aromatic. The polycarbonate macroglycols typically have a molecular weight of between about 200 and about 4000 Daltons.

Diisocyanate reactants according to this invention have the general structure OCN—R'—NCO, wherein R' is a hydrocarbon that may include aromatic or nonaromatic structures, including aliphatic and cycloaliphatic structures. Exemplary isocyanates include the preferred methylene diisocyanate (MDI), or 4,4-methylene bisphenyl isocyanate, or 4,4'-diphenylmethane diisocyanate and hydrogenated methylene diisocyanate (HMDI). Other exemplary isocyanates include hexamethylene diisocyanate and other toluene diisocyanates such as 2,4-toluene diisocyanate and 2,6-toluene diisocyanate, 4,4' tolidine diisocyanate, m-phenylene diisocyanate, 4-chloro-1,3-phenylene diisocyanate, 4,4-tetramethylene diisocyanate, 1,6-hexamethylene diisocyanate, 1,10-decamethylene diisocyanate, 1,4-cyclohexylene diisocyanate, 4,4'-methylene bis (cyclohexylisocyanate), 1,4-isophorone diisocyanate, 3,3'-dimethyl-4,4'-diphenylmethane diisocyanate, 1,5-tetrahydronaphthalene diisocyanate, and mixtures of such diisocyanates. Also included among the isocyanates applicable to this invention are specialty isocyanates containing sulfonated groups for improved hemocompatibility and the like.

Suitable chain extenders included in this polymerization of the polycarbonate urethanes should have a functionality that is equal to or greater than two. A preferred and well-recognized chain extender is 1,4-butanediol. Generally speaking, most diols or diamines are suitable, including the ethylenediols, the propylenediols, ethylenediamine, 1,4-butanediamine methylene dianiline heteromolecules such as ethanolamine, reaction products of the diisocyanates with water and combinations of the above.

The polycarbonate urethane polymers according to the present invention should be substantially devoid of any significant ether linkages (i.e., when, y is 0, 1 or 2 as represented in the general formula hereinabove for a polycarbonate macroglycol), and it is believed that ether linkages should not be present at levels in excess of impurity or side reaction concentrations. While not wishing to be bound by any specific theory, it is presently believed that ether linkages account for much of the degradation that is experienced by polymers not in accordance with the present invention due to enzymes that are typically encountered in vivo, or otherwise, attack the ether linkage via oxidation. Live cells probably catalyze degradation of polymers containing linkages. The polycarbonate urethanes useful in the present invention avoid this problem.

Because minimal quantities of ether linkages are unavoidable in the polycarbonate producing reaction, and because these ether linkages are suspect in the biodegradation of polyurethanes, the quantity of macroglycol should be minimized to thereby reduce the number of ether linkages in the polycarbonate urethane. In order to maintain the total number of equivalents of hydroxyl terminal groups approximately equal to the total number of equivalents of isocyanate terminal groups, minimizing the polycarbonate soft segment necessitates proportionally increasing the chain extender hard segment in the three component polyurethane system. Therefore, the ratio of equivalents of chain extender to macroglycol should be as high as possible. A consequence of increasing this ratio (i.e., increasing the amount of chain extender with respect to macroglycol) is an increase in hardness of the polyurethane. Typically, polycarbonate urethanes of hardnesses, measured on the Shore scale, less than 70A show small amounts of biodegradation. Polycarbonate urethanes of Shore 75A and greater show virtually no biodegradation.

The ratio of equivalents of chain extender to polycarbonate and the resultant hardness is a complex function that includes the chemical nature of the components of the urethane system and their relative proportions. However, in general, the hardness is a function of the molecular weight of both chain extender segment and polycarbonate segment and the ratio of equivalents thereof. Typically, the 4,4'-methylene bisphenyl diisocyanate (MDI) based systems, a 1,4-butanediol chain extender of molecular weight 90 and a polycarbonate urethane of molecular weight of approximately 2000 will require a ratio of equivalents of at least about 1.5 to 1 and no greater than about 12 to 1 to provide non-biodegrading polymers. Preferably, the ratio should be at least about 2 to 1 and less than about 6 to 1. For a similar system using a polycarbonate glycol segment of molecular weight of about 1000, the preferred ration should be at least about 1 to 1 and no greater than about 3 to 1. A polycarbonate glycol having a molecular weight of about 500 would require a ratio in the range of about 1.2 to about 1.5:1.

The lower range of the preferred ratio of chain extender to macroglycol typically yields polyurethanes of Shore 80A hardness. The upper range of ratios typically yields polycarbonate urethanes on the order of Shore 75D. The preferred elastomeric and biostable polycarbonate urethanes for most medical devices would have a Shore hardness of approximately 85A.

Generally speaking, it is desirable to control somewhat the cross-linking that occurs during polymerization of the polycarbonate urethane polymer. A polymerized molecular weight of between about 80,000 and about 200,000 Daltons, for example on the order of about 120,000 Daltons (such molecular weights being determined by measurement according to the polystyrene standard), is desired so that the resultant polymer will have a viscosity at a solids content of 43% of between about 900,000 and about 1,800,000 centipoise, typically on the order of about 1,000,000 centipoise. Cross-linking can be controlled by avoiding an isocyanate-rich situation. Of course, the general relationship between the isocyanate groups and the total hydroxyl (and/or amine) groups of the reactants should be on the order of approximately 1 to 1. Cross-linking can be controlled by controlling the reaction temperatures and shading the molar ratios in a direction to be certain that the reactant charge is not isocyanate-rich; alternatively a termination reactant such as ethanol can be included in order to block excess isocyanate groups which could result in cross-linking which is greater than desired.

Concerning the preparation of the polycarbonate urethane polymers, they can be reacted in a single-stage reactant charge, or they can be reacted in multiple states, preferably in two stages, with or without a catalyst and heat. Other components such as antioxidants, extrusion agents and the like can be included, although typically there would be a tendency and preference to exclude such additional components when a medical-grade polymer is being prepared.

Additionally, the polycarbonate urethane polymers can be polymerized in suitable solvents, typically polar organic solvents in order to ensure a complete and homogeneous reaction. Solvents include dimethylacetamide, dimethylformamide, dimethylsulfoxide toluene, xylene, m-pyrrol, tetrahydrofuran, cyclohexanone, 2-pyrrolidone, and the like, or combinations thereof. These solvents can also be used to delivery the polymers to the ePTFE layer of the present invention.

A particularly desirable polycarbonate urethane is the reaction product of polyhexamethylenecarbonate diol, with methylene bisphenyl diisocyanate and the chain extender 1,4-butanediol.

The use of the elastomeric bonding agent in solution is particularly beneficial in that by coating the surface 19 of ePFTE layer 14, the bonding agent solution enters the pores 18 of layer 14 defined by the IND of the ePTFE layer. As the ePTFE is a highly hydrophobic material, it is difficult to apply a bonding agent directly to the surface thereof. By providing a bonding agent which may be disposed within the micropores of the ePFTE structure, enhanced bonding attachment between the bonding agent and the ePFTE surface is achieved.

The bonding agents of the present invention, particularly the materials noted above and, more particularly, polycarbonate urethanes, such as those formed from the reaction of aliphatic macroglycols and aromatic or aliphatic diisocyanates, are elastomeric materials which exhibit elastic properties. Conventional ePTFE is generally regarded as an inelastic material, i.e., even though it can be further stretched, it has little memory. Therefore, conventional ePTFE exhibits a relatively low degree of longitudinal compliance. Also, suture holes placed in conventional ePTFE structures do not self-seal, due to the inelasticity of the ePTFE material. By applying an elastomeric coating to the ePTFE structure, both longitudinal compliance and suture hole sealing are enhanced.

In a preferred embodiment, the elastomeric boding agent may contribute to re-sealable qualities, or puncture-sealing characteristics of the composite structure. If the bonding agent is a highly elastic substance, this may impart re-sealable quantities to the composite structure. This is especially desirous in order to seal a hole created by a suture, or when the self-sealing graft may be preferably used as a vascular access device. When used as an access device, the graft allows repeated access to the blood stream through punctures, which close after removal of the penetrating member (such as, e.g., a hypodermic needle or cannula) which provided the access.

The ePTFE self-sealing graft can be used for any medical technique in which repeated hemoaccess is required, for example, but without intending to limit the possible applications, intravenous drug administration, chronic insulin injections, chemotherapy, frequent blood samples, connection to artificial lungs, and hyperalimentation. The self-sealing ePTFE graft is ideally suited for use in chronic hemodialysis access, e.g., in a looped forearm graft fistula, straight forearm graft fistula, an axillary graft fistula, or any other AV fistula application. The self-sealing capabilities of the graft are preferred to provide a graft with greater suture retention, and also to prevent excessive bleeding from a graft after puncture (whether in venous access or otherwise).

Referring again to FIG. 1, textile layer 12 is secured to surface 19 of ePTFE layer 14 which has been coated with bonding agent 20. The textile layer 12 is secured by placing it in contact with the bonding agent. As it will be described in further detail hereinbelow, this process can be performed either by mechanical, chemical or thermal techniques or combinations thereof.

The composite prosthesis 10 may be used in various vascular applications in planar form as a vascular patch or in tubular form as a graft. The textile surface may be designed as a tissue contacting surface in order to promote enhanced cellular ingrowth which contributes to the long term patency of the prosthesis. The ePTFE surface 14 may be used as a blood contacting surface so as to minimize leakage and to provide a generally anti-thrombogetic surface. While this is the preferred usage of the composite prosthesis of the present invention, in certain situations, the layers may be reversed where indicated.

The present invention provides for various embodiments of composite ePTFE/textile prosthesis.

Figure 2:
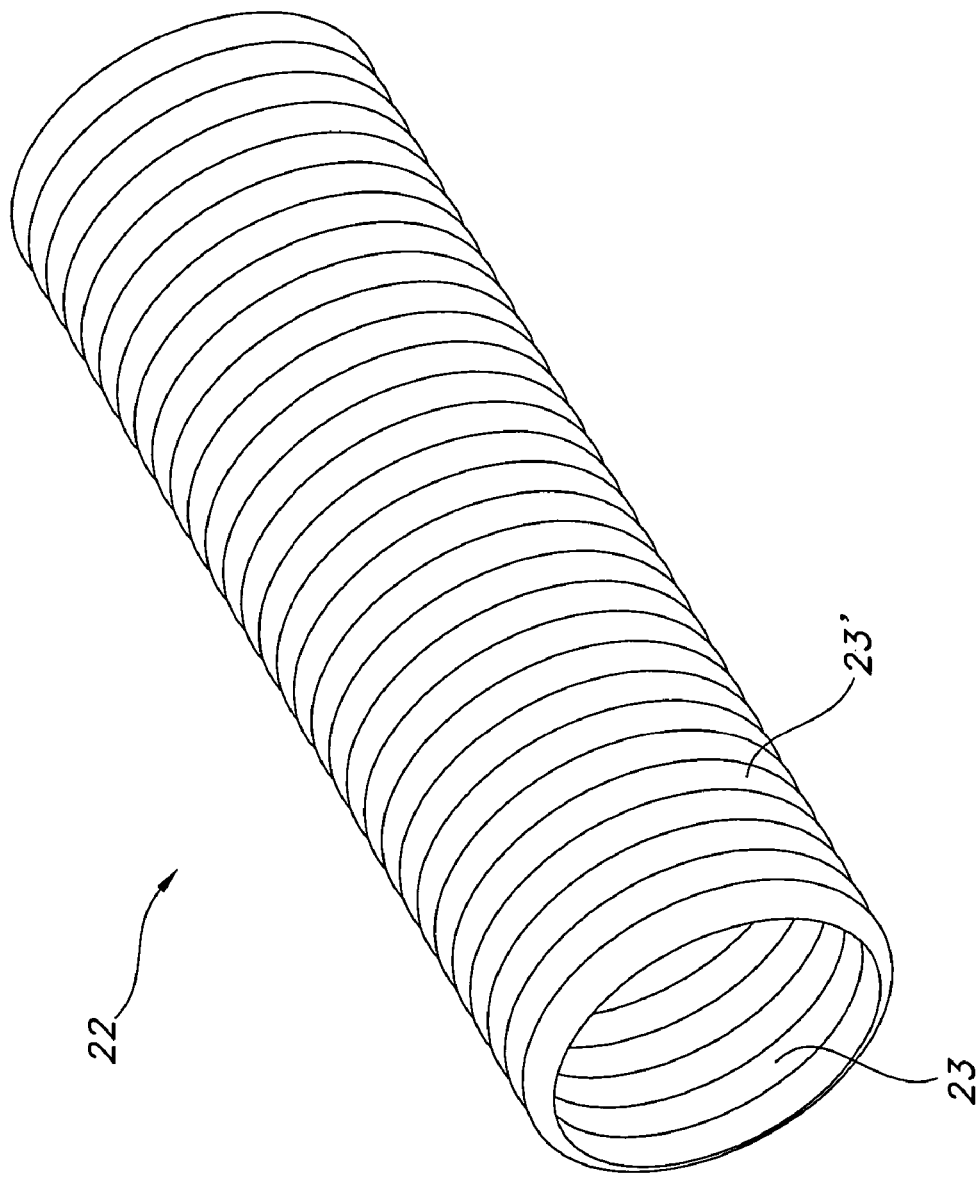
FIGS. 2 and 3 show an ePTFE-lined textile grafts of the present invention.
Figure 3:
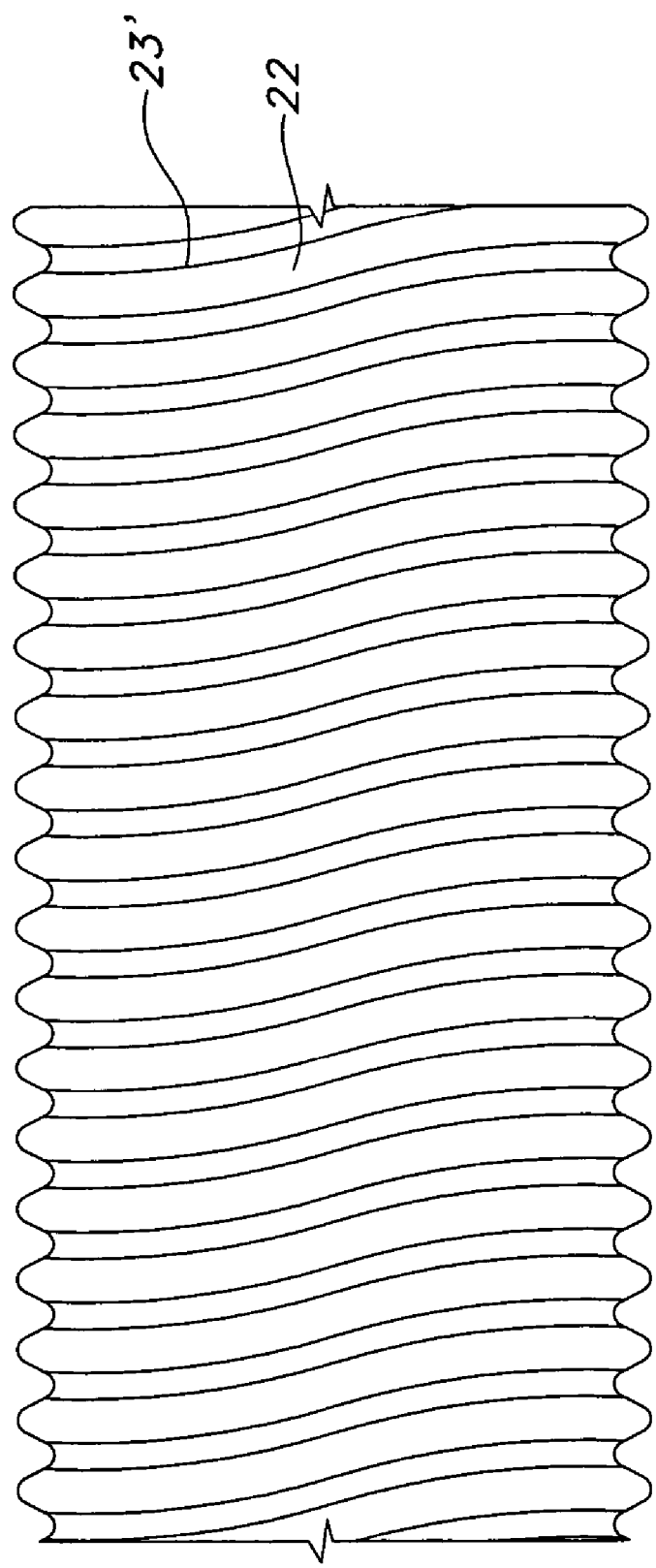

With reference to FIGS. 2 and 3, a ePTFE-lined textile graft 22 is shown. Graft 22 includes an elongate textile tube having opposed inner and outer surfaces 23, 23'. As the graft 22 of the present invention is a composite of ePTFE and textile, the textile tube may be formed thinner than is traditionally used for textile grafts. A thin-walled liner of an ePTFE tube is applied to the internal surface of the textile tube to form the composite graft. The ePTFE liner reduces the porosity of the textile tube so that the textile tube need not be coated with a hemostatic agent such as collagen which is typically impregnated into the textile structure. The overall wall thickness of composite graft 22 is thinner than an equivalent conventional textile grafts.

While the composite graft 22 of FIGS. 2 and 3 employs the ePTFE liner on the internal surface of the textile tube, it of course may be appreciated that the ePTFE liner may be applied to the exterior surface of the textile tube.

The composite ePTFE-lined textile graft is desirably formed as follows. A thin ePTFE tube is formed in a conventional forming process such as by tubular extrusion or by sheet extrusion where the sheet is formed into a tubular configuration. The ePTFE tube is placed over a stainless steel mandrel and the ends of the tube are secured. The ePTFE tube is then spray coated with an adhesive solution of anywhere from 1%-15% Corethane® urethane range, 2.5 W30 in DMAc. As noted above, other adhesive solutions may also be employed. The coated ePTFE tube is placed in an oven heated in a range from 64° F. (18° C.) to 302° F. (150° C.) for 5 minutes to overnight to dry off the solution. If desired, the spray coating and drying process can be repeated multiple times to add more adhesive to the ePTFE tube. The coated ePTFE tube is then covered with the textile tube to form the composite prosthesis. One or more layers of elastic tubing, preferably silicone, are then placed over the composite structure. This holds the composite structure together and assures that complete contact during the subsequent pressure lamination of the present invention. The assembly of the composite graft within the elastic tubing is placed in an oven and heated in a range of 325° F.-425° F. (163° C.-218° C.) for approximately 5-30 minutes to bond the layers together.

Thereafter, the ePTFE lined textile graft may be crimped along the tubular surface thereof to impart longitudinal compliance, kink resistance and enhanced handling characteristics. The crimp may be provided by placing a coil of metal or plastic wire around a stainless steel mandrel. The graft 22 is slid over the mandrel and the coil wire. Another coil is wrapped around the assembly over the graft to fit between the spaces of the inner coil. The assembly is then heat set and results in the formation of the desired crimp pattern. It is further contemplated that other conventional crimping processes may also be used to impart a crimp to the ePTFE textile graft.

In order to further enhance the crush and kink resistance of the graft, the graft can be wrapped with a polypropylene monofilament. This monofilament is wrapped in a helical configuration and adhered to the outer surface of the graft either by partially melting the monofilament to the graft or by use of an adhesive.

The ePTFE-lined textile graft exhibits advantages over conventional textile grafts in that the ePTFE liner acts as a barrier membrane which results in less incidences of bleeding without the need to coat the textile graft in collagen. The wall thickness of the composite structure may be reduced while still maintaining the handling characteristics, especially where the graft is crimped. A reduction in suture hole bleeding is seen in that the elastic bonding agent used to bond the textile to the EPTE, renders the ePTFE liner self-sealing.

Figure 4:
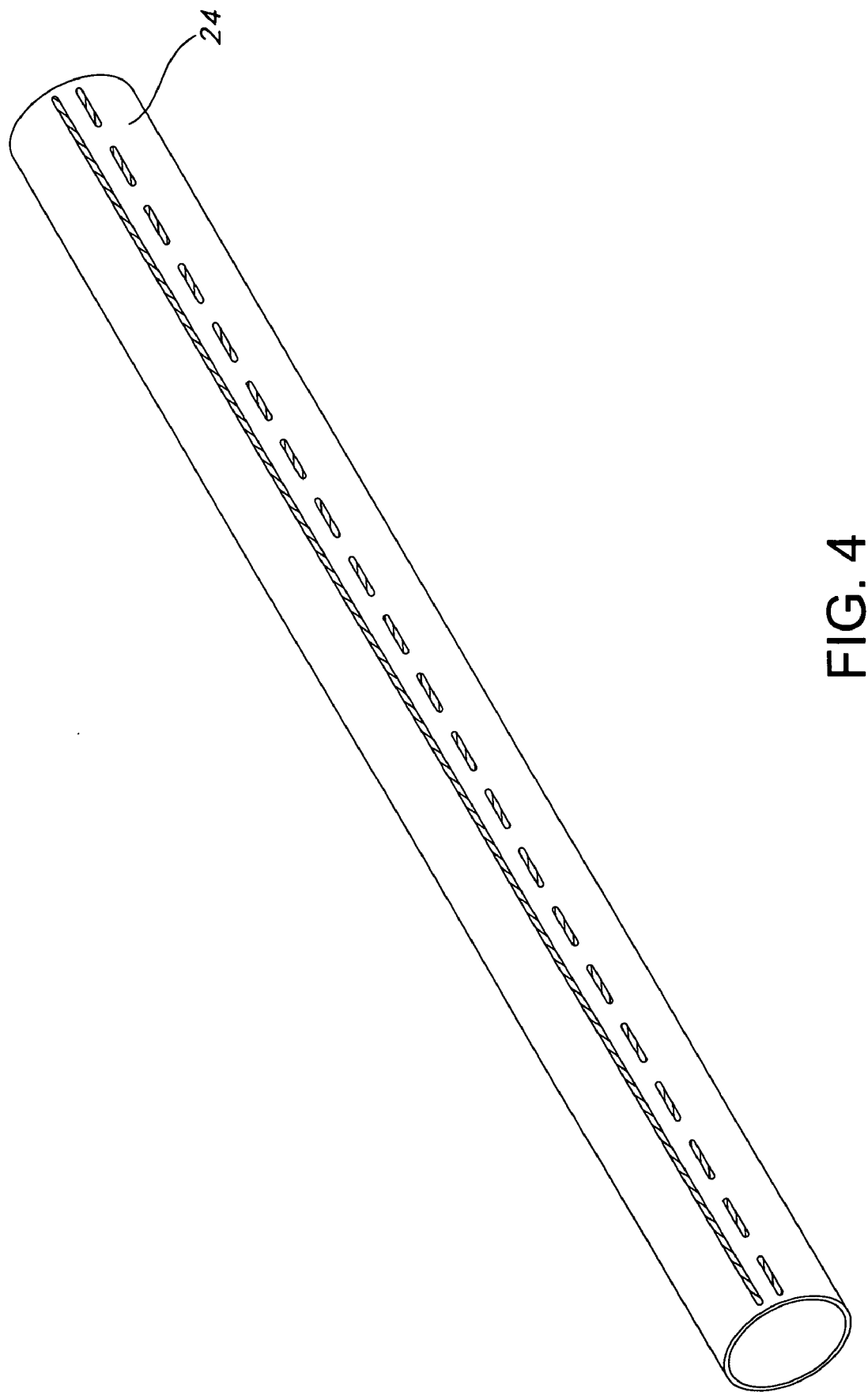
FIGS. 4, 5 and 6 show an ePTFE; graft with a textile coating of the present invention.
Figure 5:
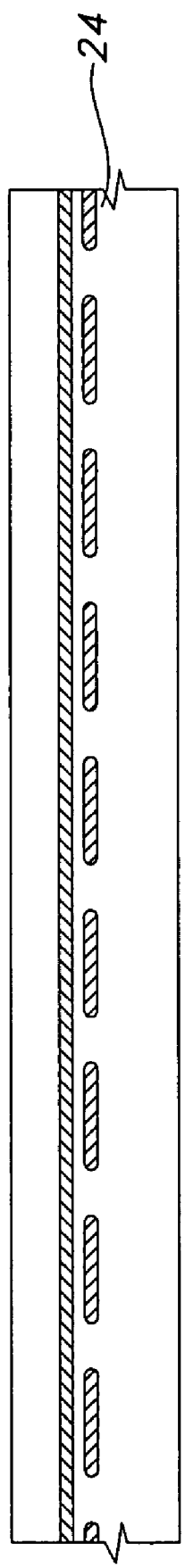
Figure 6:
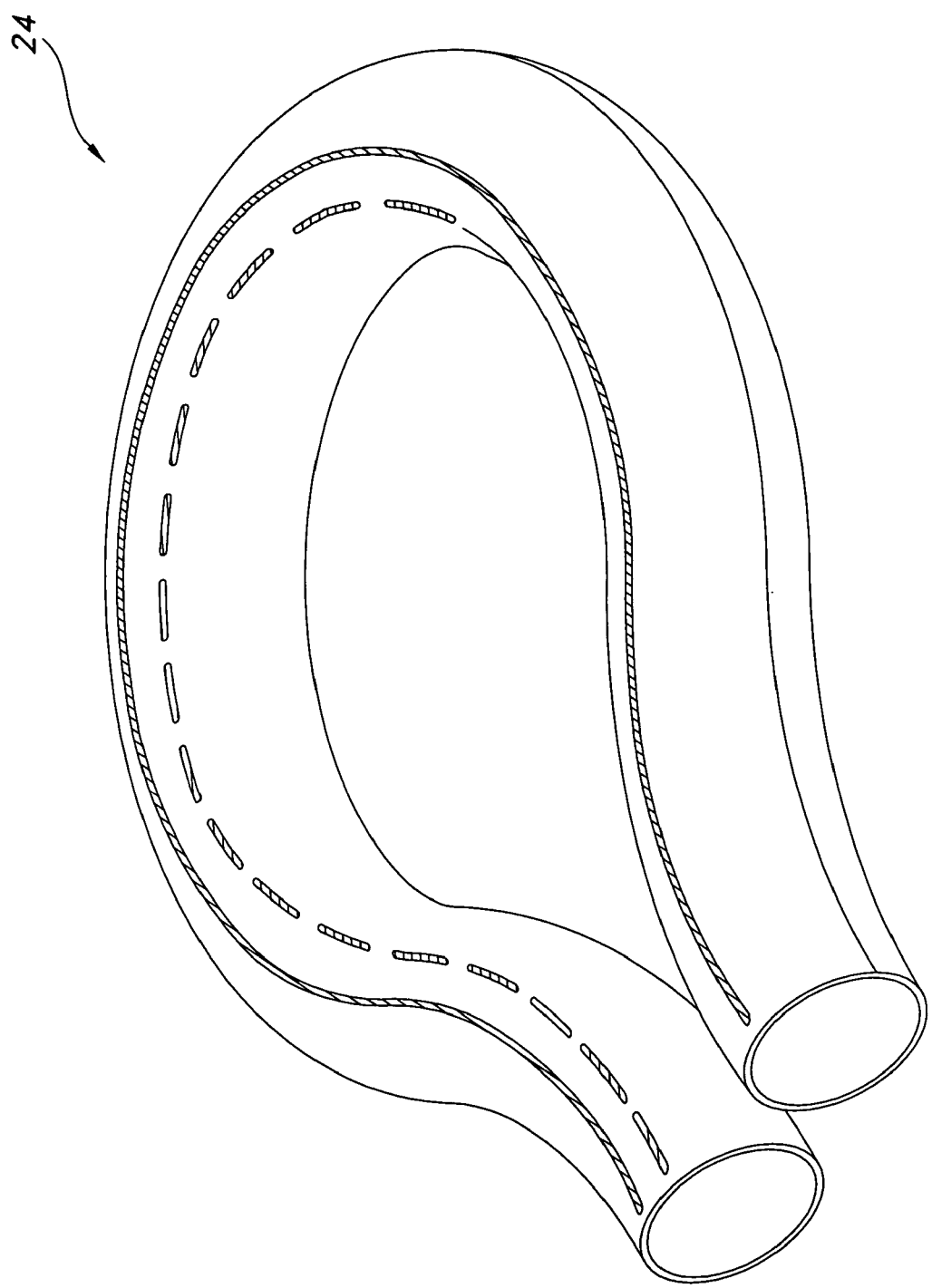
Figure 7:
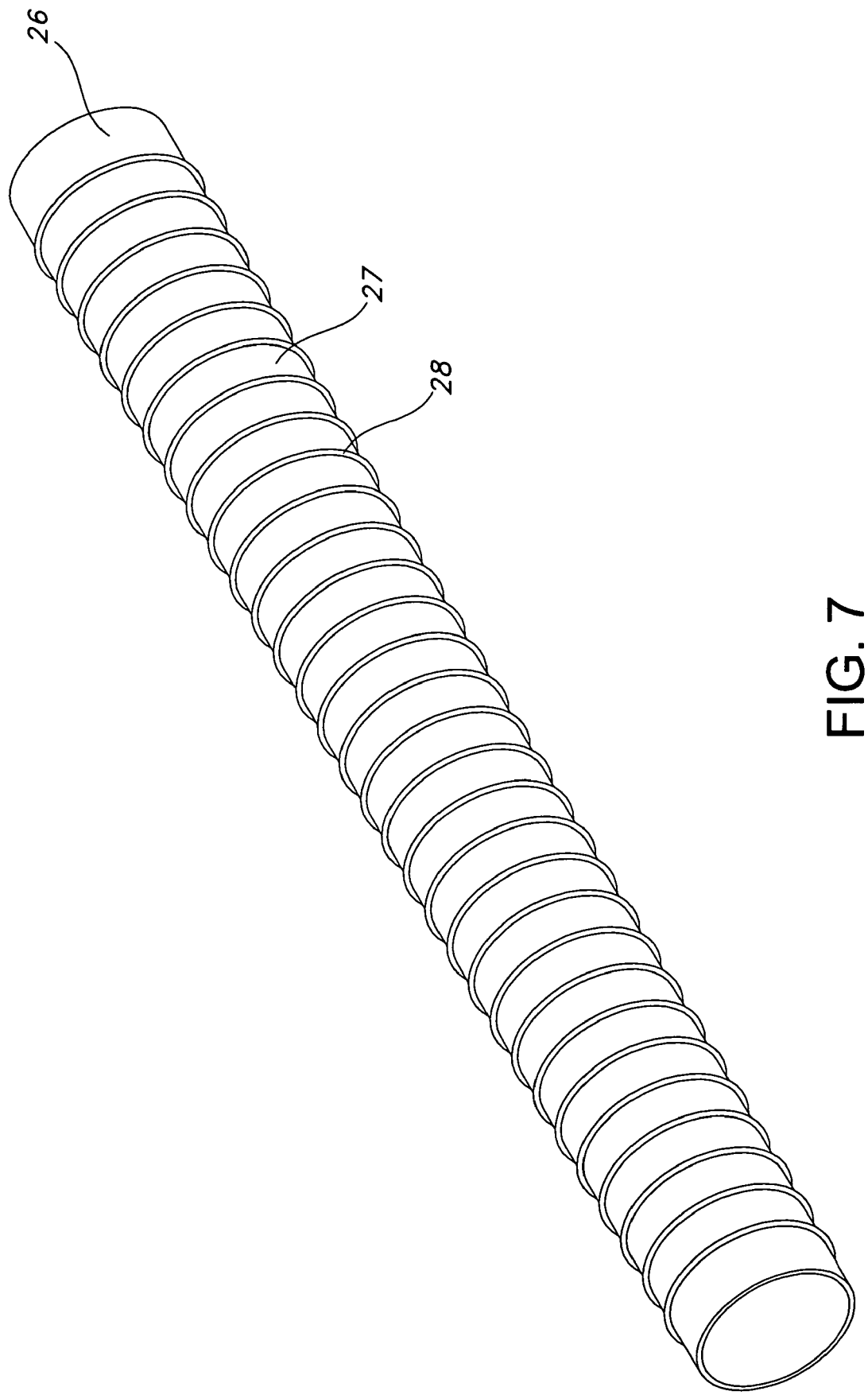
FIGS. 7-10 show the ePTFE graft with a textile coating of FIG. 4 with an external coil applied thereto.
Figure 8:
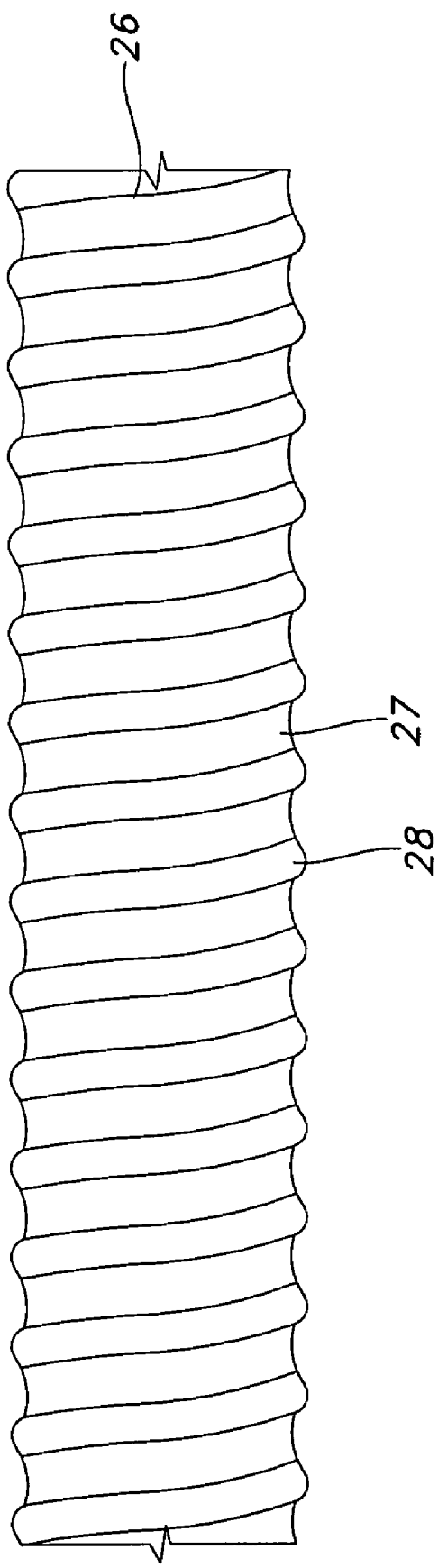
Figure 9:
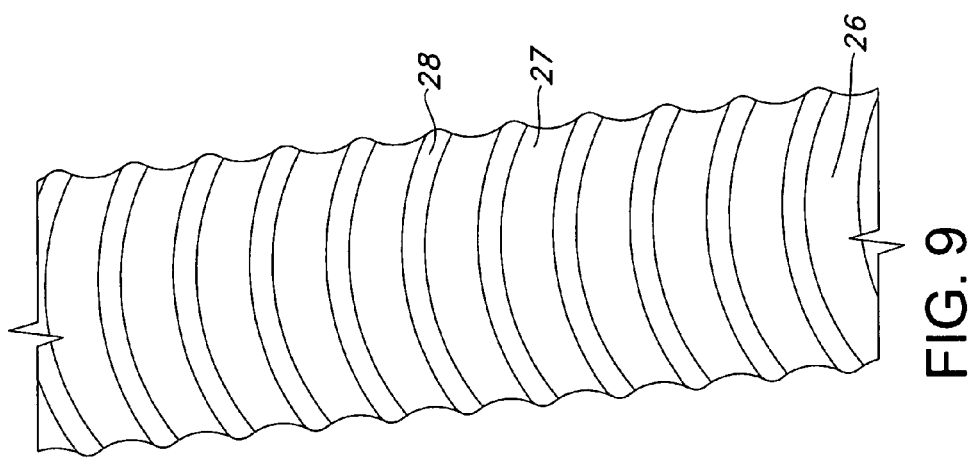
Figure 10:
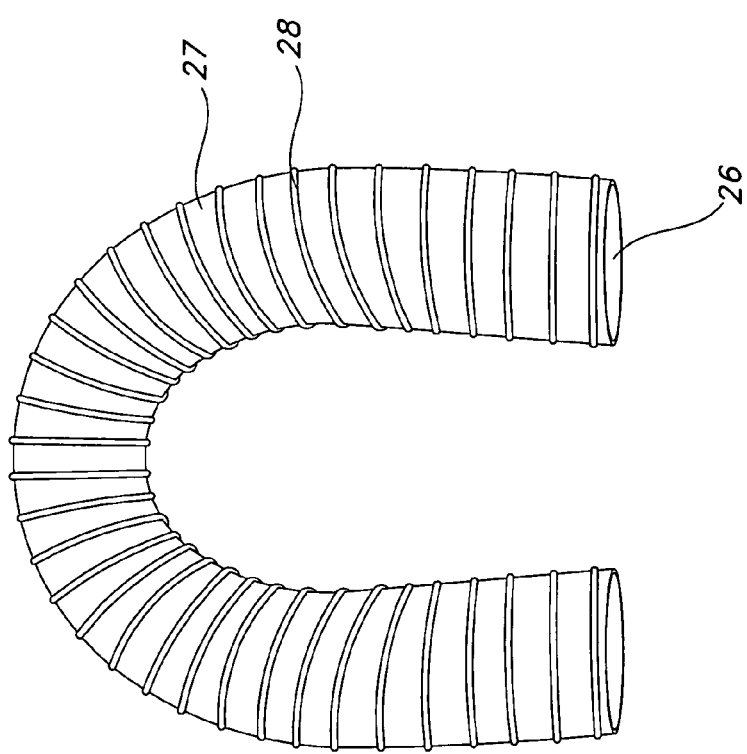

Referring now FIGS. 4, 5 and 6, a further embodiment of the composite ePTFE textile prosthesis of the present invention is shown. A textile covered ePTFE vascular graft 24 is shown. Graft 24 includes an elongate ePTFE tube having positioned thereover a textile tube. The ePTFE tube is bonded to the textile tube by an elastomeric bonding agent.

The process for forming the textile covered ePTFE vascular graft may be described as follows.

An ePTFE tube formed preferably by tubular paste extrusion is placed over a stainless steel mandrel. The ends of the ePTFE tube are secured. The ePTFE tube is coated using an adhesive solution of anywhere from 1%-15% range Corethane®, 2.5 W30 and DMAc. The coated ePTFE tubular structure is then placed in an oven heated in a range from 18° C. to 150° C. for 5 minutes to overnight to dry off the solution. The coating and drying process can be repeated multiple times to add more adhesive to the ePTFE tubular structure.

Once dried, the ePTFE tubular structure may be longitudinally compressed in the axial direction to between 1% to 85% of its length to coil the fibrils of the ePTFE. The amount of desired compression may depend upon the amount of longitudinal expansion that was imparted to the base ePTFE green tube to create the ePTFE tube. Longitudinal expansion and compression may be balanced to achieve the desired properties. This is done to enhance the longitudinal stretch properties of the resultant graft. The longitudinal compression process can be performed either by manual compression or by thermal compression.

The compressed ePTFE tube is then covered with a thin layer of the textile tube. One or more layers of elastic tubing, preferably silicone, is placed over the composite. This holds the composite together and assures that there is complete contact and adequate pressure. The assembly is then placed in a 325-425° F. oven for approximately 10-20 minutes to bond the layers together.

As noted above and as shown in FIGS. 7-10, the composite graft 26 can be wrapped with a polypropylene monofilament 28 which is adhered to the outer surface 27 by melting or use of an adhesive. The polypropylene monofilament will increase the crush and kink resistance of the graft. Again, the graft can be crimped in a convention manner to yield a crimped graft.

The textile covered ePTFE graft exhibits superior longitudinal strength as compared with conventional ePTFE vascular grafts. The composite structure maintains high suture retention strength and reduced suture hole bleeding. This is especially beneficial when used as a dialysis access graft in that the composite structure has increased strength and reduced puncture bleeding. This is achieved primarily by the use of an elastomeric bonding agent between the textile tubular structure and the ePTFE tubular structure in which the elastic bonding agent has a tendency to self-seal suture holes.

Figure 11:
FIGS. 11-13 show a composite ePTFE textile vascular patch of the present invention.
Figure 12:
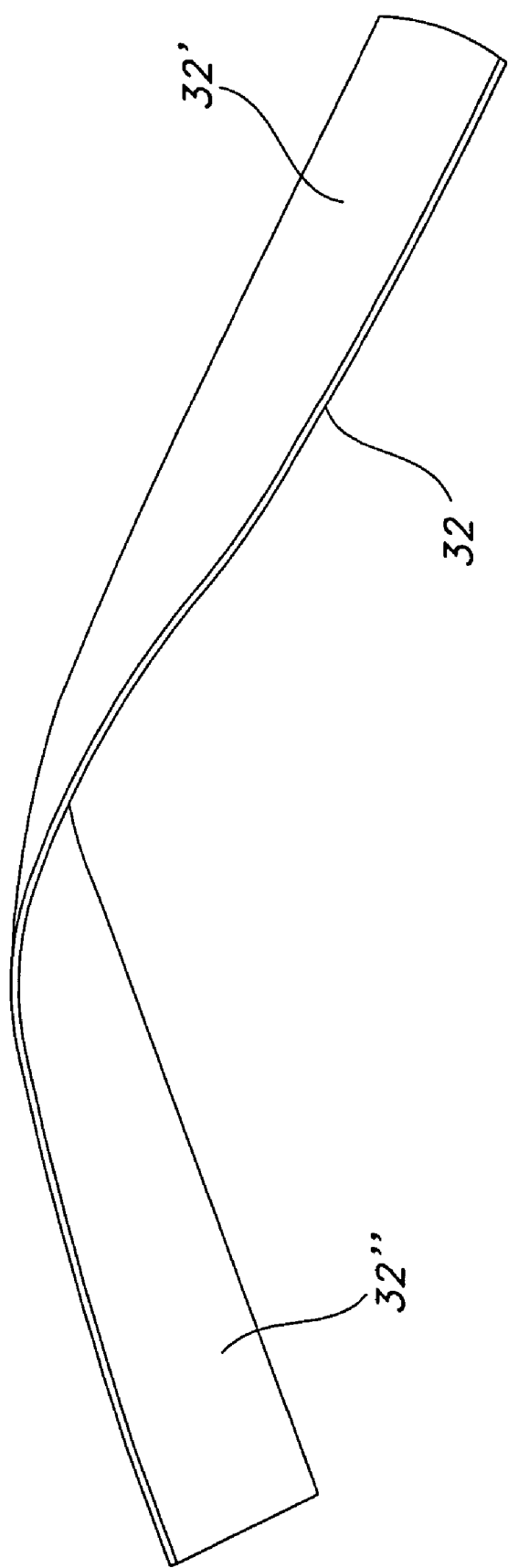
Figure 13:
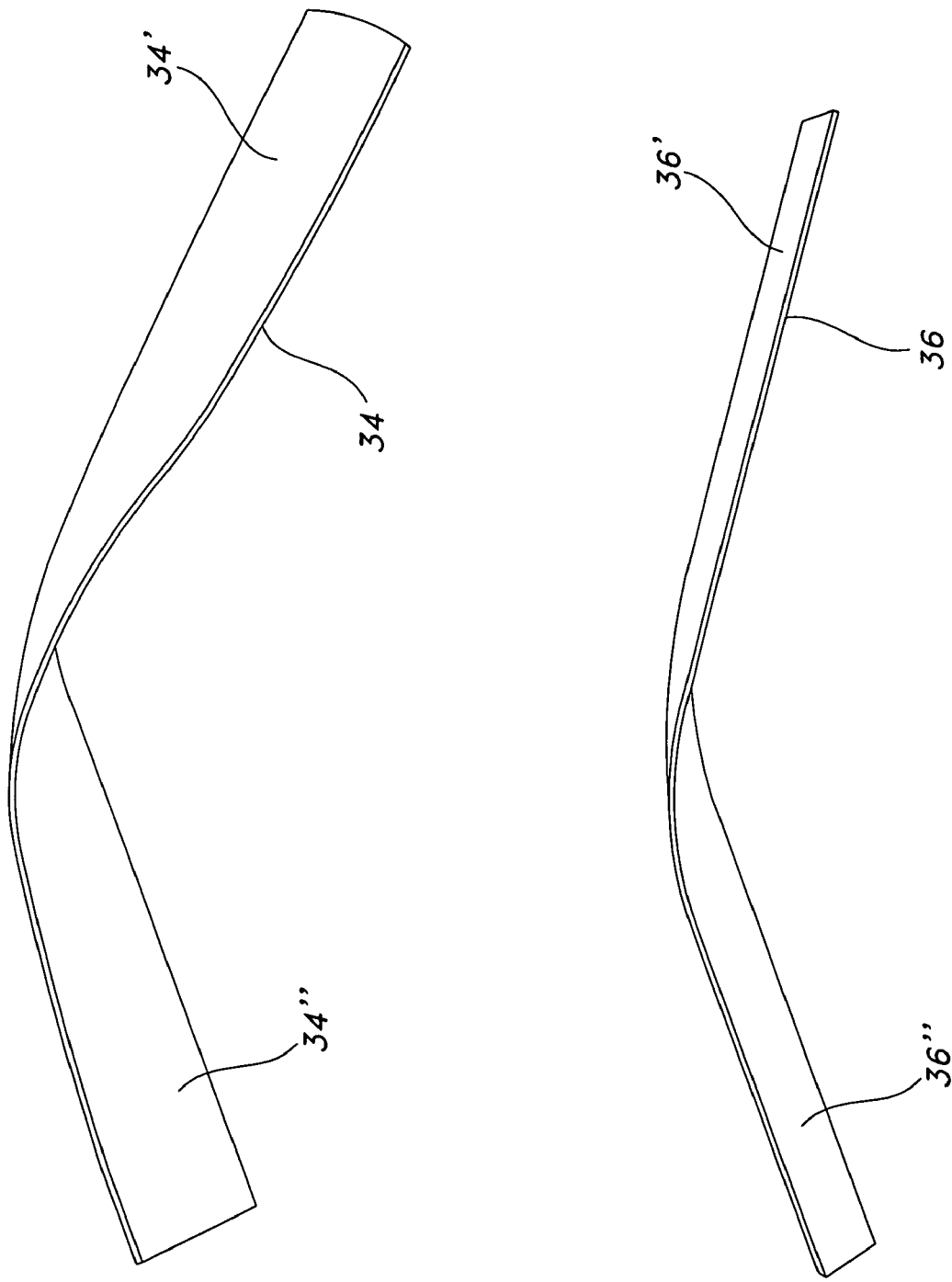

Referring now to FIGS. 11-13, a textile reinforced ePTFE vascular patch 30, 32, 34, 36 is shown. The vascular patch 30, 32, 34, 36 of the present invention is constructed of a thin layer of membrane of ePTFE which is generally in an elongate planar shape. The ePTFE membrane is bonded to a thin layer of textile material which is also formed in an elongate planar configuration. The ePTFE layer is bonded to the textile layer by use of an elastomeric bonding agent. The composite structure can be formed of a thickness less than either conventional textile or ePTFE vascular patches. This enables the patch to exhibit enhanced handling characteristics.

Vascular patch 30 includes a layer of ePTFE 30' and a textile layer 30" of stretch polyester, such as Dacron™. Vascular patch 32 includes a layer of ePTFE 32' and a textile layer 32" of a velour fabric. Vascular patch 34 includes a layer of ePTFE 34' and a textile reinforced layer 34" of stretch polyester. The stretch polyester may be a textile fabric having stretchable yarn, such as partially drawn polyester or PET, a textile fabric having stretchability because of the textile pattern used, such as a high-stretch-warp-knitted pattern, or combinations thereof. Vascular patch 36 includes a layer of ePTFE 36' and a textile reinforced layer 36" of a single velour fabric.

As is well known, the vascular patch may be used to seal an incision in the vascular wall or otherwise repair a soft tissue area in the body. The ePTFE surface of the vascular patch would be desirably used as the blood contacting side of the patch. This would provide a smooth luminal surface and would reduce thrombus formation. The textile surface is desirably opposed to the blood contacting surface so as to promote cellular ingrowth and healing.

The composite vascular patch may be formed by applying the bonding agent as above described to one surface of the ePTFE layer. Thereafter, the textile layer would be applied to the coated layer of ePTFE. The composite may be bonded by the application of heat and pressure to form the composite structure. The composite vascular patch of the present invention exhibits many of the above stated benefits of using ePTFE in combination with a textile material. The patches of the present invention may also be formed by first making a tubular construction and then cutting the requisite planar shape therefrom.

Figure 14:
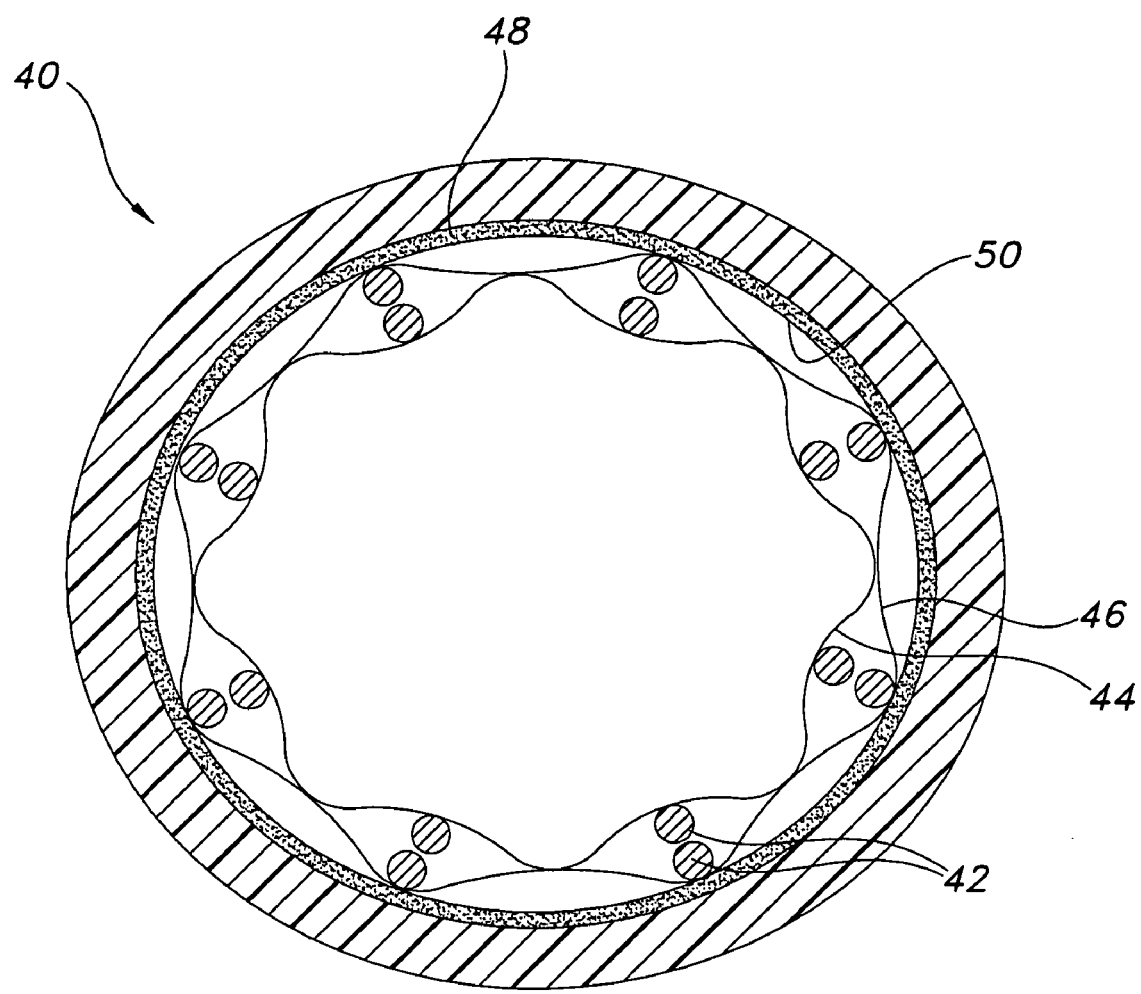
FIGS. 14 and 15 show a schematic cross-section of a composite stent-graft of the resent invention.
Figure 15:
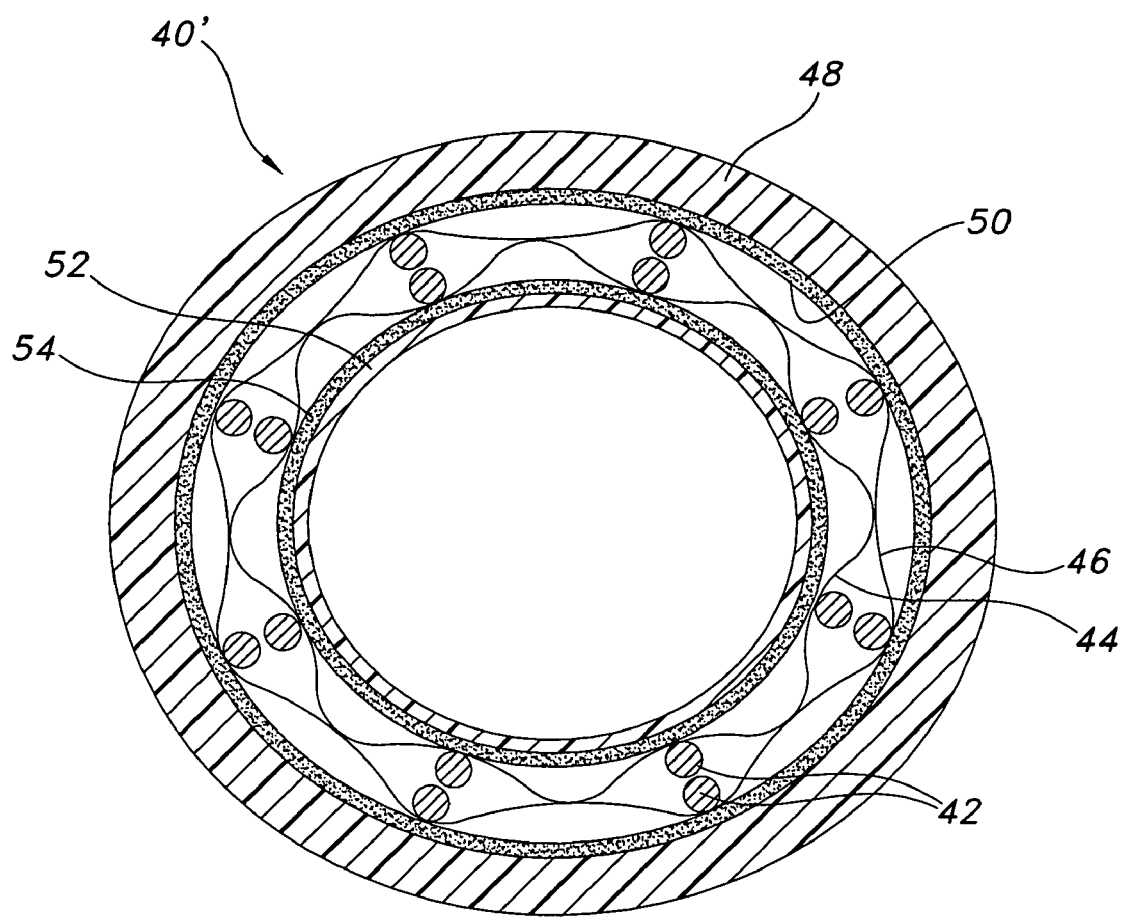

With reference to FIGS. 14 and 15, various embodiments of a multi-layered composite grafts are depicted. With reference to FIG. 14, a composite graft 40 is shown having a tubular support structure 42 interposed between inner and outer ePTFE layers 44 and 46. The ePTFE layers 44 and 46 are joined using any technique known to those skilled in the art, such as by sintering or with an adhesive (thermoplastic fluoropolymer adhesive (FEP)). The ePTFE layers 44, 46 are joined through interstices found in the support structure 42, preferably without being affixed to the support structure 42. The outer ePTFE layer 46 is bonded to a textile layer 48 with a layer of bonding agent 50. The arrangement of the layers may be altered, wherein the support structure 42 and the ePTFE layers 44, 46 may be disposed externally of the textile layer 48 with the layer of bonding agent 50 being interposed between the textile layer 48 and the inner ePTFE layer 44. The composite graft is formed to allow for simultaneous radial expansion of the support structure 42 along with the ePTFE layers 44, 46 and the textile layer 48. The radial expansion is preferably unhindered by any of the constituent elements of the composite graft.

The tubular support structure 42 may be any structure known in the art which is capable of maintaining patency of the composite graft 40 in a bodily vessel. For example, the support structure 42 may be a stent, and preferably is radially-expandable. Radially-expandable member 42 may be of any stent configuration known to those skilled in the art, including those used alone or in a stent/graft arrangement. Various stent types and stent constructions may be employed in the present invention including, without limitation, self-expanding stents and balloon expandable stents. The stents may be capable of radially contracting as well. Self-expanding stents include those that have a spring-like action which cause the stent to radially expand or stents which expand due to the memory properties of the stent material for a particular configuration at a certain temperature. Nitinol® is an example of a material which may be used as a self-expanding stent. Other materials are of course contemplated, such as stainless steel, platinum, gold, titanium, tantalum, niobium, and other biocompatible materials, as well as polymeric stents. The configuration of the stent may also be chosen from a host of geometries. For example, wire stents can be fastened in a continuous helical pattern, with or without wave-like forms or zigzags in the wire, to form a radially deformable stent. Individual rings or circular members can be linked together such as by struts, sutures, or interlacing or locking of the rings to form a tubular stent. Although a wide variety of distensible members may be used, FIG. 14 shows one particular distensible member 42, a stent, which may be employed in prosthesis 40. The particular stent shown in FIG. 14 is more fully described in commonly assigned U.S. Pat. No. 5,693,085 to Buirge et al., the disclosure of which is incorporated by reference herein.

With reference to FIG. 15, an alternative embodiment of the composite graft 40 is shown therein and designated generally with the reference numeral 40'. Like numbers are used to designate like elements. With this embodiment, an additional inner textile reinforcement 52 is provided which is fixed by an inner layer of bonding agent 54.

The textile layers 48, 52 and the bonding agent layers 50, 54 may be of any structure described in the embodiments above. Likewise, the interaction between the ePTFE layers, the textile layers, and the bonding agent 50, 54 is the same interaction described above.

FIG. 16 is a perspective, partial cut-away view of prosthesis 60 of the present invention. Prosthesis 60 is a hollow tubular structure having a tubular wall 62. As depicted in FIG. 17, which is a cross-sectional view of the prosthesis 60 of FIG. 16, tubular wall 62 includes an outer layer of textile portion 64 and an inner layer of ePTFE 66. Textile portion 64 may include any suitable synthetic yarns, such as those yarns previously described in conjunction with textile material 12. Desirably, the textile portion 64 and the ePTFE portion 66 are adhesively joined to form a unitary composite tubular wall 62.

The textile portions of the present invention can have virtually any textile construction, including weaves, knits, braids, filament windings and the like. Useful weaves include, but are not limited to, simple weaves, basket weaves, twill weaves, satin weaves, velour weaves and the like. Useful knits include, but are not limited to, high stretch knits, locknit knits (also referred to as tricot or jersey knits), reverse locknit knits, sharkskin knits, queenscord knits and velour knits. Useful high stretch, warp-knitted patterns include those with multiple patterns of diagonally shifting yarns, such as certain modified atlas knits which are described in U.S. Pat. No. 6,540,773, the contents of which are in incorporated herein by reference. Other useful high-stretch, warp knitted patterns include certain patterns with multiple needle underlap and one needle overlap, such as those patterns described in U.S. Pat. No. 6,554,855 and U.S. Patent Application Publication No. 2003/0204241 A1, the contents of which are incorporated herein by reference.

FIGS. 18 and 19 depict another embodiment of the present invention in which like numbers are used to designate like elements. Prosthesis 60' includes a tubular wall 62' which is a composite wall structure having a textile portion 64 disposed over a stent 68 which in turn is disposed over the ePTFE portion 66. The present invention, however, is not so limited. For example, textile portion 64 may be disposed over ePTFE portion 66 which may be disposed over interior and/or exterior surfaces of stent 68 (not shown).

FIGS. 20 and 21 depict yet another embodiment of the present invention in which like numbers are used to designate like elements. Prosthesis 60" includes a tubular wall 62" which is a composite wall structure having a textile portion 64 disposed over an ePTFE portion 66', disposed over stent 68 disposed over ePTFE portion 66.

The tubular prostheses 60, 60' and 60" of the present invention are formed into unitary composite tubular devices through the pressure lamination method of the present invention. The tubular prostheses 60, 60' and 60" may be pressure laminated with use of a hollow mandrel 70. FIG. 22 is a perspective view of hollow mandrel 70. Hollow mandrel 70 is an elongate hollow tubular member having an open end 72 and a closed end 74 with a hollow bore 76 therebetween. As depicted in FIG. 23A, a plurality of holes 78 extend through wall 80 of the tubular mandrel 70 to provide fluid communication to the hollow bore 76. Desirably, as depicted in FIG. 23B, the closed end 74 is fluid tight without a bore or hole extending therethrough. The hollow mandrel 70 may be constructed of any suitable material that can process the lamination temperatures and pressures of the present invention without substantial deformation. Desirably, the hollow mandrel 70 is made from a stainless steel metal or material. Although hollow mandrel 70 is depicted as having a substantially smooth surface 82, the present invention is not so limited. Mandrel 70 may have a pattern of depressions or raised surfaces which may, for example, correspond to the open cell geometry (not shown) of stent 68. Additionally, the present invention is not limited to the use of a hollow mandrel 70 with a plurality of holes 78. A hollow mandrel with one hole 78 may suitably be used.

As depicted in FIGS. 24-28, in which like numbers are used to designate like elements, the tubular prostheses 62, 62' and 62" of the present invention are disposed over the plurality of holes 78 extending through the wall 80 of the hollow mandrel 70. An elastic barrier material 84 is placed over the prostheses 62, 62' and 62" to initially align the components of the prostheses which are to be laminated together. Barrier material 84 is desirably a hollow tubular silicone member, but other materials and shapes may suitably be used, such as, but not limited to, strips of elastic material which may be wound over the prostheses to initially align and secure the components thereof. Desirably, the barrier material 84 substantially covers the exterior surface of prostheses 62, 62' and 62" when positioned on the mandrel 70. The barrier material need not provide a complete fluid tight barrier over the prosthesis, but a fluid tight barrier may suitably be used.

As depicted in FIGS. 24-26, bonding agent 20 may be disposed over surfaces of components that are to be laminated together. For example, as depicted in FIGS. 24 and 26 bonding agent 20 may be disposed between textile layer 64 and ePTFE layer 66 or 66'. As depicted in FIGS. 25 and 26, bonding agent 20 may be used to form composite stent-graft devices by bonding layers exterior and interior to the stent 68 to one and the other. Although bonding agent 20 is depicted as completely surrounding stent 68 in FIGS. 25 and 26, the present invention is not so limited. Opposed layers interior and exterior to the stent 68 may be securely joined without adhesively filling the open spaces of stent 28, as discussed above in conjunction with FIGS. 14 and 15.

Figure 27:
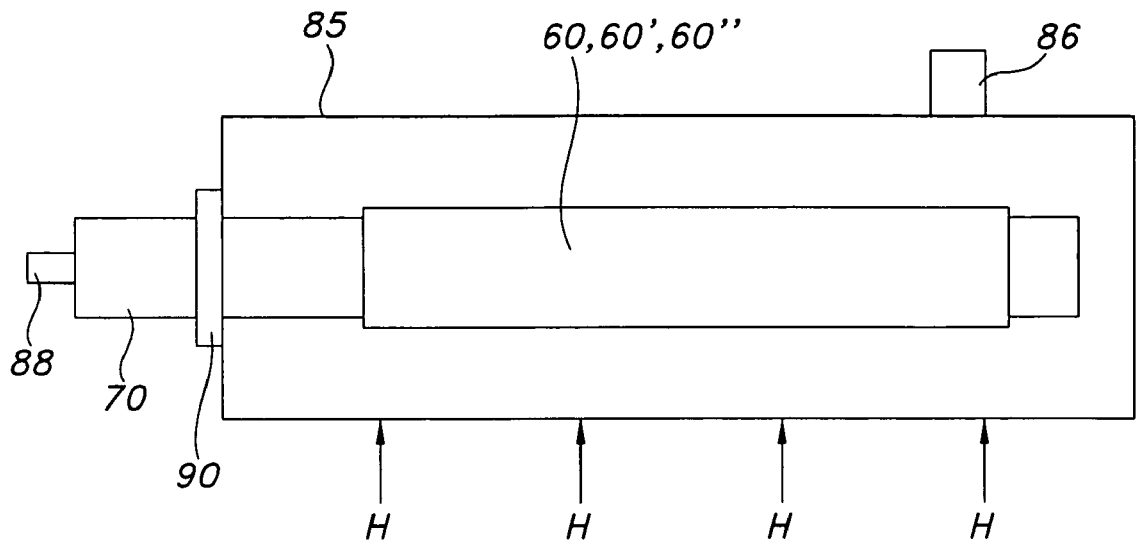
FIGS. 27 and 28 show a schematic view of a pressurizable chamber useful for pressure lamination of tubular prostheses of the present invention.

As depicted in FIG. 27, portions of the mandrel 70 containing the prosthesis 60, 60' and 60" may be sealably disposed within a hollow member 85. Member 85 may be of any useful shape. Tubular shape members are advantageously used. Hollow member 85 includes a pressure inlet port 86 where gas, such as air or nitrogen may be supplied to provide and maintain a positive pressure within the member 85. Hollow mandrel 70 may have a pressure controlling means 88 at its open end to further assist in maintaining a positive pressure with the hollow member 85. Further, hollow member 85 may include a seal 90 to provide a fluid tight seal over the mandrel 70 to further assist in maintaining a pressure differential during lamination.

Desirably, the pressure within the member 85 is higher than the pressure outside the member 85. In other words, the pressure within hollow member 85 external to the prostheses 60, 60' and 60" should be greater than the pressure within the hollow bore 76 of mandrel 70, thereby defining a positive pressure differential. Thus, member 85 functions as a pressure chamber in which pressure may be controlled. Desirably, the positive pressure differential is from about 1 to about 50 pounds per square inch absolute (psia), preferably from about 1 to about 10 psia, such as from about 1 psia to about 50 psia.

Member 85 containing the hollow mandrel 70 and the prostheses 60, 60' and 60" may be placed proximal or within a source of heat. For example, the member 85 may be placed within an oven (not shown) where the member 85 and prostheses 60, 60' and 60" are heated by convection, as indicated by vectors "H". Desirably, the prostheses 60, 60' and 60" and the bonding agent 20 contained therein are heated to a temperature of about 325° F. to about 450° F. to cure the bonding agent 20 and to adhesively laminate prosthesis components.

Figure 28:
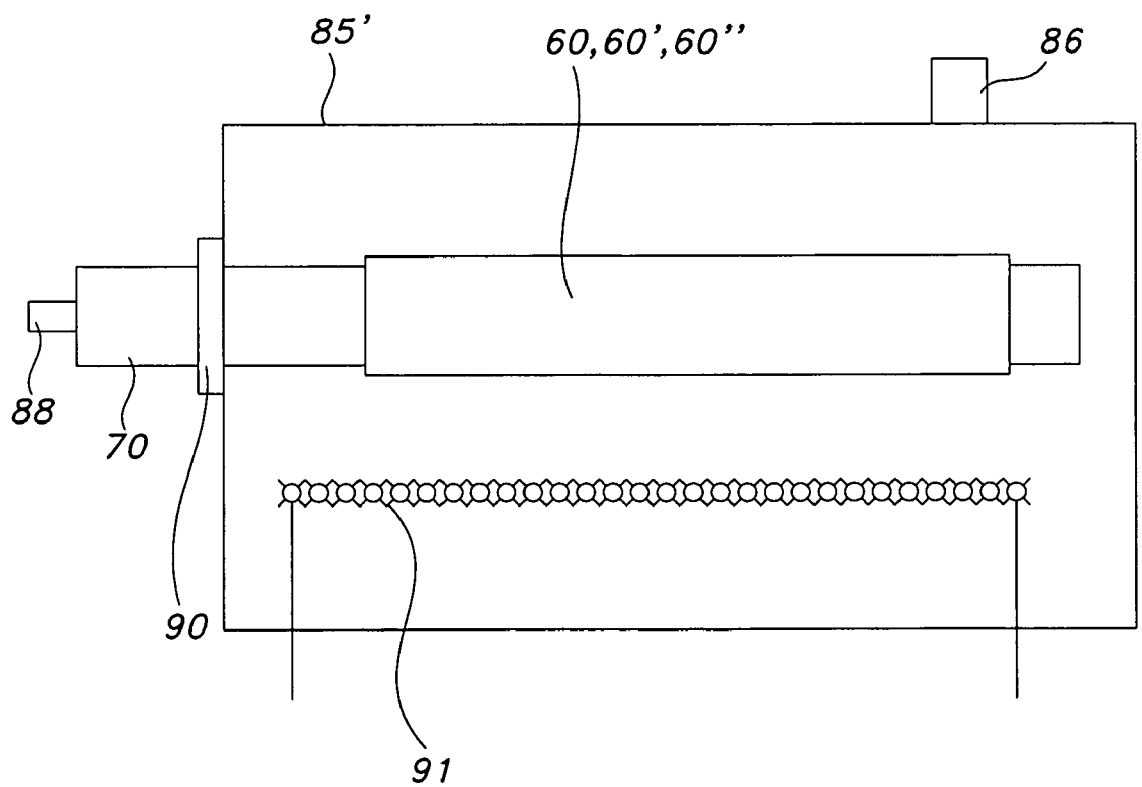

Alternatively, as depicted in FIG. 28, hollow member 85' may contain a heating element 91 therein to provide the enthalpy for effecting cure of the bonding agent 20.

The use of the positive pressure differential is useful in providing desired bond strength and desired bond strength uniformity. Without the use of the positive pressure differential the thickness and shape of barrier member 84 would have to be experimentally altered to provide adequate bonding pressures. In other words, a thicker or more highly stretched elastic member would have to be placed over the prosthesis and mandrel to adequately bond the components of the prosthesis, and this would unnecessarily complicate the bonding technique and would still not necessarily ensure even distribution of applied pressure over different portions of the prosthesis.

The applied pressure lamination method of the present invention provides a laminated composite prosthesis with improved bond strength and bond uniformity among the laminated components. For example, the composite prosthesis of the present invention has a bond shear strength of at least 4.5 g/mm$^2$ (grams force per mm of sample circumference per mm of sample length tested) which is substantially higher than a composite prosthesis formed from non-pressurized lamination techniques. Desirably, the composite prosthesis of the present invention has a bond shear strength of from about 4.5 g/mm$^2$ to about 7.0 g/mm$^2$, more desirably from about 5.0 g/mm$^2$ to about 5.5 g/mm$^2$. Such bond shear strengths are substantially improved over the prior art. For example, comparable composite prostheses that were laminated with the techniques of the prior have bond shear strengths of much less than 4.5 g/mm$^2$, for example 4.3 g/mm or less. Typically, the prosthesis of the present invention exhibit a 15% to 35% increase in the bond shear strength over the prior art. For example, prostheses of the present invention desirably have from about 20% to 25% greater shear bond strength as compared to the prior art. Further, the variability of the bond shear strengths is improved for the composite prostheses as compared to composite prostheses of the prior art. The standard deviation of the bond shear strengths along the length of the device for the composite prostheses of the present invention is less than about 2, for example from about 1 to about 1.3. Composite prostheses of the prior art typically have a standard variation of greater than 2, for example about 4 or twice the variation.

Further, the applied pressure lamination method of the present invention provides a laminated composite prosthesis with improved bond peel strength and uniformity among the laminated components. For example, the composite prosthesis of the present invention has a bond peel strength of at least 32 g/mm (grams force per mm of sample width tested) which is substantially higher than a composite prosthesis formed from non-pressurized lamination techniques. Desirably, the composite prosthesis of the present invention has a bond peel strength of from about 32 g/mm to about 40 g/mm, more desirably from about 35 g/mm to about 39 g/mm. Such bond peel strengths are substantially improved over the prior art. For example, comparable composite prostheses that were laminated with the techniques of the prior have bond peel strengths of much less than 32 g/mm, for example 31.3 g/mm or less. Typically, the prosthesis of the present invention exhibit a 5% to 30% increase in the bond peel strength over the prior art. For example, prostheses of the present invention desirably have from about 15% to 20%, or greater bond peel strength as compared to the prior art. Further, the variability of the bond peel strengths is improved for the composite prostheses as compared to composite prostheses of the prior art. The standard deviation of the bond shear strengths along the length of the device for the composite prostheses of the present invention is less than about 4, for example from about 3 to about 4, preferably from about 3.5. Composite prostheses of the prior art typically have a standard variation that is greater than 4, for example about 5 or greater.

Still further, the composite prostheses of the present invention have greater water impermeability as compared to similar devices in the prior art. For example, at about 3 psi (or 155 mm Hg) of water the composite devices of the present invention have a water porosity of less than 0.05 ml/cm$^2$/min, for example about 0.02 to about 0.04 ml/cm$^2$/min, preferably about 0.03 ml/cm$^2$/min. Composite devices of the prior art typically have a water porosity at 3 psi (or 155 mm Hg) of 0.10 ml/cm$^2$/min or greater, for example typically about 0.15 ml/cm$^2$/min. Typically, the composite devices of the present invention have w water porosity that is from about 70% to about 90% lower than comparable devices of the prior art, preferably from about 75% to about 85% lower. Further, the composite devices of the present invention exhibit no separation, such as separation of the ePTFE/textile composite layer from the stent, at 3 psi (or 155 mm Hg) as compared to the devices of the prior art which exhibited gross separation. At higher pressures the improvements of the present invention are similarly noted. For example, at about 5 psi (or 258 mm Hg) of water the composite devices of the present invention have a water porosity of less than 0.3 ml/cm$^2$/min, for example about 0.1 to about 0.3 ml/cm$^2$/min, preferably about 0.26 ml/cm$^2$/min. Composite devices of the prior art typically have a water porosity at 5 psi (or 258 mm Hg) of 0.6 ml/cm$^2$/min or greater, for example typically about 0.64 ml/cm$^2$/min. Typically, the composite devices of the present invention have a water porosity that is from about 50% to about 70% lower than comparable devices of the prior art, preferably from about 55% to about 65% lower. Further, the composite devices of the present invention exhibit no separation, such as separation of the ePTFE/textile composite layer from the stent, at 5 psi (or 258 mm Hg) as compared to the devices of the prior art which exhibited gross separation.

Figure 29:
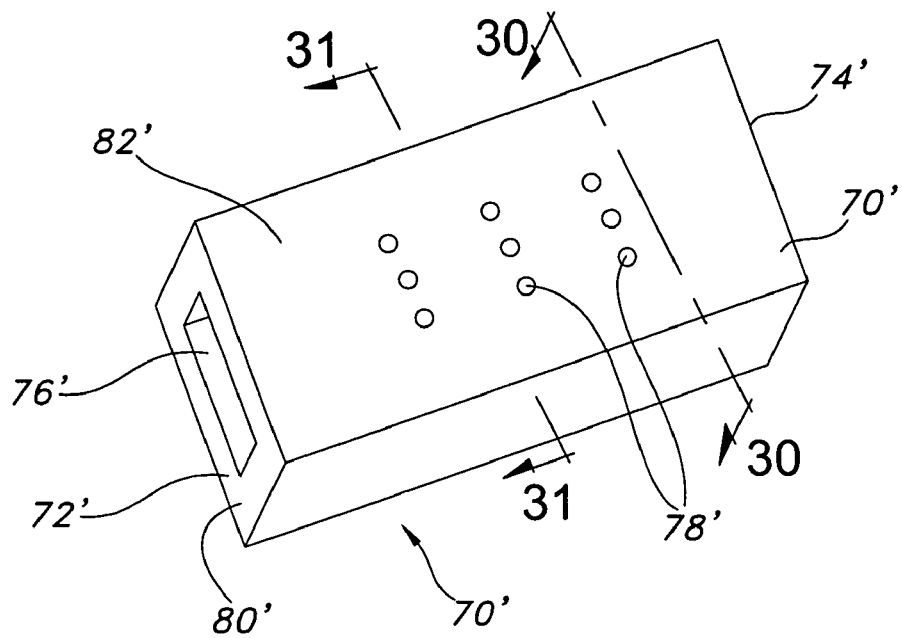
FIG. 29 shows a perspective view of a hollow plate useful for pressure lamination of vascular patches of the present invention.
Figure 30:
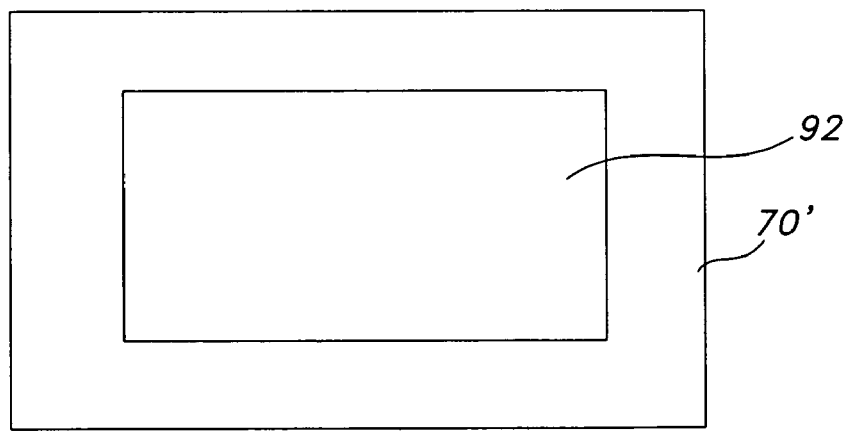
FIGS. 30 and 31 show a top view and a cross-sectional view of a vascular patch disposed on the hollow plate of FIG. 29.
Figure 31:
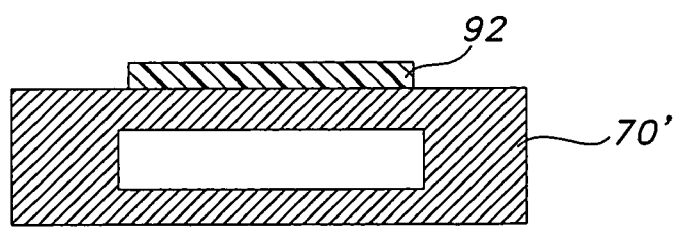

With reference to FIG. 29, an alternative embodiment of the hollow mandrel 70 is shown therein where like numbers are used to designate like elements and is designated generally with the reference number 70' which depicts a hollow and planar or flat member 70'. The flat member 70' is useful for pressure lamination of a vascular patch 92 as depicted in FIGS. 30 and 31.

In one aspect of the present invention, a method of forming a composite textile and ePTFE implantable device is provided. The method includes the steps of (a) providing an ePTFE layer having opposed surfaces comprising a microporous structure of nodes interconnected by fibrils; (b) providing a textile layer having opposed surfaces; (c) applying a coating of an elastomeric bonding agent to one of the opposed surfaces of the ePTFE layer or the textile layer; (d) providing a hollow member having an open end and an opposed closed end defining a fluid passageway therebetween and having a wall portion with at least one hole extending therethrough, the hole being in fluid communication with the fluid passageway; (e) concentrically placing the ePTFE layer and the textile layer onto the hollow member and over the at least one hole of the hollow member to provide an interior composite layer and an exterior composite layer, thereby defining a composite assembly, wherein the interior composite layer is one of the ePTFE layer or the textile layer and the exterior composite layer is the other of the ePTFE layer or the textile layer; (f) placing the hollow member with the composite assembly within a pressure chamber; (g) applying a pressure differential so that the pressure within the chamber is greater than a pressure within the fluid passageway of the hollow member; and (h) applying heat to the bonding agent to adhesively bond the textile layer and the ePTFE layer to provide a laminated composite assembly.

The method of this aspect of the present invention may further include applying a solution of the bonding agent, or alternatively spray coating the surface of the ePTFE layer with the solution. Desirably, the bonding agent is dried prior to the concentric placement of the assembly components. This provide for better bonding control of the agent and also avoid undesirable migration of the bonding agent, such as onto or into the hollow member or mandrel. Further, the method of the present invention advantageously pressure laminates the assembly components without the need for a mass flowable particulate to effectuate adequate bonding or lamination.

In another aspect of the present invention, the textile layer is a hollow tubular textile layer having an inner and outer textile surface and the ePTFE layer is applied to the inner textile surface. Further, the ePTFE layer may be a hollow tubular structure. Desirably, such an implantable device is a vascular prosthesis. Alternatively, a vascular prosthesis may be provided where the textile layer is a hollow tubular textile layer having an inner and outer textile surface and the ePTFE layer is applied to the outer textile surface.

The pressure lamination method of present invention may further include the step of applying an elastic barrier member over an exterior surface of the exterior composite layer. The elastic barrier may be adjacently disposed over the exterior surface of the exterior composite layer. The elastic barrier may also be adjacently disposed over the exterior surface of the exterior composite layer without applying a flowable mass particulate therebetween.

Desirably, the applied pressure differential is from about 1 psia to about 10 psia, and the step of applying heat to the bonding agent includes heating the bonding agent from about 350° F. to about 450° F.

Further, the step of applying the coating of the elastomeric bonding agent may include the step of applying the coating to one of the opposed surfaces of the ePTFE layer with the bonding agent being disposed within the microporous structure.

In another embodiment of the present invention, the pressure lamination method may further include the steps of providing a distensible stent; and placing the distensible stent between the textile layer and the ePTFE layer. The method may further include the step of providing a second layer of ePTFE between the stent and the textile layer. Further, the method may include the steps of providing a distensible stent; and placing the distensible stent onto the hollow member prior to the step of placing the ePTFE layer and the textile layer onto the hollow member.

Useful bonding agents with the pressure lamination of the present invention include urethanes, styrene/isobutylene/styrene block copolymers, silicones, and combinations thereof. Further, the textile layer may be a knitted textile layer, a woven textile layer, a stretch-knit textile layer, a braided textile layer, and combinations thereof.

The method of the present invention is also for providing a composite vascular patch where the textile layer and the ePTFE layer are substantially planar.

In another aspect of the present invention, a composite vascular prosthesis is provided. The prosthesis includes a tubular ePTFE structure having a microporous structure of nodes interconnected by fibrils; a tubular textile structure; and a cured elastomeric bonding agent adhesively securing the ePTFE structure and the textile structure; where the textile structure and the ePTFE structure are pressure laminated to provide the composite prosthesis having a bond shear strength of at least 5 kilograms (kg) and a variation or standard deviation of the bond strength of less than 0.3 kg. Such an inventive prosthesis has at least about 20 increased bond shear strength as compared to similar composite devices of the prior art. The prosthesis may further include a distensible stent, where the stent is disposed on an exterior surface of the tubular ePTFE structure, disposed on an exterior surface of the tubular textile structure, or disposed between the tubular textile structure and the tubular ePTFE structure.

With any embodiment of the composite graft 40, 40', 60', 60" an implantable prosthesis may be formed which is self-supporting and usable to maintain patency of a bodily vessel, such as in the coronary vasculature, esophagus, trachea, colon, biliary tract, urinary tract, prostate, and brain. Also, the composite graft 40, 40', 60', 60" may be treated with any of the following: anti-thrombogenic agents (such as heparin, heparin derivatives, urokinase, and PPack (dextrophenylalanine proline arginine chloromethylketone); anti-proliferative agents (such as enoxaprin, angiopeptin, or monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); anti-neoplastic/antiproliferative/anti-miotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl keton, an RGD peptide-containing compound, heparin, antithrombin compounds, platelet receptor antagonists, anti-thrombin antibodies, anti-platelet receptor antibodies, aspirin, prostaglandin inhibitors, platelet inhibitors and tick antiplatelet peptides); vascular cell growth promotors (such as growth factor inhibitors, growth factor receptor antagonists, transcriptional activators, and translational promotors); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vascoactive mechanisms.

The invention may be further understood with reference to the following non-limiting examples.

EXAMPLES

Example 1

Textile/ePTFE Prosthesis

Textile and ePTFE prosthesis components were pressured laminated in accordance with the present invention to provide a pressure-laminated prosthesis. The pressure laminated device was compared to a similar device, i.e., a control, prepared without pressure lamination.

Single layered textile grafts were prepared by knitting PET yarns in a two-needle underlap and a one-needle overlap to provide a high stretch tubular graft having a nominal internal diameter of about 13 mm. High stretch ePTFE: tubular members having a nominal tubular diameter of about 13 mm were also prepared. The ePTFE tubular members had a wall thickness of about 175 to about 225 microns. Straight or linear ePTFE tubular members or constructs had from about 800 or greater percent longitudinal expansibility. Bifurcated ePTFE tubular members or constructs had from about 2,000 percent or greater longitudinal expansibility. Corethane® was applied as an adhesive bonding agent to secure the textile portions to the ePTFE.

ePTFE tubular members were placed over a hollow tubular mandrels of about 13 mm in diameter and having a plurality of holes through its wall. Corethane® was then sprayed over the ePTFE. A textile graft was then placed over the ePTFE. A thin silicone tube of about 0.5 to 1.25 mm in thickness and a diameter of about 8 to 10 mm was placed inside a hollow tube of about 19 mm in diameter. A vacuum was applied to the tube to expand the silicone tube to about 19 mm. The expanded silicone tube was placed over the textile portion and the vacuum was released so that the silicone tube covered the prosthesis components. One set of prosthesis components were pressure laminated at 374° F. for ten minutes at about a 2.5 psi applied positive pressure differential, and another set of prosthesis components were pressure laminated at 374° F. for ten minutes at about a 5 psi applied positive pressure differential to provide pressure-laminated composite prostheses of the present invention.

A control was also prepared using the same prosthesis components and adhesive. The control ePTFE and control textile graft were placed over a 13 mm diameter mandrel. Two silicone tubes were placed over the control components by the above-described technique. The two silicone tubes applied a pressure or force of about 1 to 2 psi to the components. The control components were then laminated together at 374° F. for ten minutes.

The prostheses were also prepared with a 1 cm flap of non-bonded textile and non-bonded ePTFE. These unbonded flaps were pulled apart under control and measured force to measure the peel strength or the force required to separate the bonded textile from the bonded ePTFE. The pressure-laminated composite prostheses of the present invention had improved mechanical properties over the control, as detailed below in Table 1.

TABLE 1

Textile/ePFTE Prostheses

| Mechanical Properties | Inventive Pressure Laminated Composite Device | "Control" Laminated Composite Device |
|---|---|---|
| Bond Peel Strength[1] | | |
| grams per 19.05 mm sample width | 711 | 604 |
| standard deviation | 75 | 90 |
| % increase in bond peel strength | 18% | — |
| Bond Peel Strength[2] | | |
| grams per mm sample width | 37.2 | 31.3 |
| standard deviation | 3.5 | — |
| % increase in bond peel strength | 18% | — |

[1]Linear or straight tubular textile/ePTFE graft sample with a sample width of 19.05 mm.
[2]Linear or straight tubular textile/ePTFE graft.

The textile/ePTFE prostheses formed by the pressure lamination techniques of the present invention had improved mechanical integrity as indicated by the higher bond peel strengths and also had more consistent bond peel strengths as indicated by the lower standard deviation.

Example 2

Textile/ePTFE/Stent Prosthesis

Metal stents (Wallstent®) of about 13 mm in diameter were provided and placed on the above-described 13 mm mandrels. The composite textile/ePTFE prosthesis components from Example 1 were also used as described above (i.e., textile, Corethane® and ePTFE), except that Corethane® was also applied to the stent wires to bond the stent and the ePTFE. Textile, ePTFE and stent prosthesis components were pressured laminated in accordance with the present invention to provide a pressure-laminated prosthesis under the conditions described in Example 1 and a control was also prepared under the conditions described in Example 1.

The pressure-laminated composite prostheses of the present invention had improved mechanical properties over the control, as detailed below in Table 2.

TABLE 2

Textile/ePFTE/Stent Prostheses

| Mechanical Properties | Inventive Pressure Laminated Composite Device | "Control" Laminated Composite Device |
|---|---|---|
| Bond Shear Strength[1] | | |
| kilograms | 5.29 | 4.30 |
| standard deviation | 0.23 | 0.54 |
| % increase in bond shear strength | 23% | — |

TABLE 2-continued

Textile/ePFTE/Stent Prostheses

| Mechanical Properties | Inventive Pressure Laminated Composite Device | "Control" Laminated Composite Device |
|---|---|---|
| Bond Shear Strength[2] | | |
| grams per mm sample circumference per mm sample overlap | 6.1 | 5.0 |
| standard deviation | 1.25 | — |
| % increase in bond shear strength | 23% | — |
| Water Porosity Measurements (ml/cm²/min)[3] | | |
| at a test pressure of 3 psi (155 mm Hg) | 0.03 | 0.15 |
| at a test pressure of 5 psi (155 mm Hg) | 0.26 | 0.64 |
| Component Separation Observations[3] | | |
| Composite separation at 3 psi | No Separation | Gross Separation |
| Composite separation at 5 psi | No Separation | Gross Separation |

[1]Linear or straight tubular textile/ePTFE stent-graft sample with a sample circumference of about 40.8 mm (corresponding to a 13 mm stent outside diameter) and a 2 cm sample overlap.
[2]Linear or straight tubular textile/ePTFE stent-graft.
[3]Bifurcated textile/ePTFE stent-graft.

The textile/ePTFE/stent prostheses formed by the pressure lamination techniques of the present invention had improved mechanical integrity as indicated by the higher bond shear strengths and also had more consistent bond shear strengths as indicated by the lower standard deviation. The bond shear strength is a measurement of the force required to separate the textile/ePTFE components from the stent. Additionally, the devices were placed under internal water pressures of 3 and 5 psi. Water porosity was measured and device integrity was observed. The textile/ePTFE/stent prostheses formed by the pressure lamination techniques of the present invention had improved water porosities without component separation which also indicate improved component bonding with the techniques of the present invention.

Various changes to the foregoing described and shown structures will now be evident to those skilled in the art. Accordingly, the particularly disclosed scope of the invention is set forth in the following claims.

What is claimed is:

1. A method of forming a composite textile and ePTFE implantable device comprising the steps of:
   (a) providing an ePTFE layer having opposed surfaces comprising a microporous structure of nodes interconnected by fibrils;
   (b) providing a textile layer having opposed surfaces;
   (c) applying a coating of an elastomeric bonding agent to one of said opposed surfaces of said ePTFE layer or said textile layer;
   (d) providing a hollow member having an open end and an opposed closed end defining a fluid passageway therebetween and having a wall portion with at least one hole extending therethrough, the hole being in fluid communication with said fluid passageway;
   (e) concentrically placing said ePTFE layer and said textile layer onto said hollow member and over said at least one hole of said hollow member to provide an interior composite layer and an exterior composite layer, thereby defining a composite assembly, wherein said interior composite layer is one of said ePTFE layer or said textile layer and said exterior composite layer is the other of said ePTFE layer or said textile layer;

(f) expanding an elastic silicone barrier member;

(g) disposing the expanded elastic silicone barrier member over an exterior surface of said exterior composite layer;

(h) placing said hollow member with said composite assembly within a pressure chamber;

(i) applying a positive pressure to said chamber so that the positive pressure within said chamber is higher than a pressure outside of said chamber;

(j) applying a pressure differential so that the pressure within said chamber is greater than a pressure within said fluid passageway of said hollow member;

(k) applying heat to said bonding agent to adhesively bond said textile layer and said ePTFE layer to provide a laminated composite assembly; and (l) removing said elastic silicone barrier member from said laminated composite assembly, to provide a composite textile and ePTFE implantable device having an improved bond peel strength of at least 32 g/mm and a variation of said bond peel strength of less than about 4.

2. The method of claim 1, wherein said applying step includes:
applying a solution of said bonding agent.

3. The method of claim 2, wherein said applying step further includes:
spray coating said surface of said ePTFE layer with said solution.

4. The method of claim 1, wherein said textile layer is a hollow tubular textile layer having an inner and outer textile surface and said ePTFE layer is applied to said inner textile surface.

5. The method of claim 4, wherein said ePTFE layer is a hollow tubular structure.

6. The method of claim 4, wherein said implantable device is a vascular prosthesis.

7. The method of claim 4, further including the steps of:
providing a distensible stent; and
placing said distensible stent between said textile layer and said ePTFE layer prior to the step of placing said hollow member within said pressure chamber.

8. The method of claim 7, further including the step of providing a second layer of ePTFE between said stent and said textile layer prior to the step of placing said hollow member within said pressure chamber.

9. The method of claim 4, further including the steps of:
providing a distensible stent; and
placing said distensible stent onto said hollow member prior to the step of placing said ePTFE layer and said textile layer onto said hollow member.

10. The method of claim 1, wherein said textile layer is a hollow tubular textile layer having an inner and outer textile surface and said ePTFE layer is applied to said outer textile surface.

11. The method of claim 10, wherein said implantable device is a vascular prosthesis.

12. The method of claim 1, wherein said elastic silicone barrier is adjacently disposed over said exterior surface of said exterior composite layer.

13. The method of claim 1, wherein said elastic silicone barrier is adjacently disposed over said exterior surface of said exterior composite layer without applying a flowable mass particulate therebetween.

14. The method of claim 1, where said applied pressure differential is from about 1 psia to about 50 psia.

15. The method of claim 1, wherein the step of applying heat to said bonding agent includes heating said bonding agent from about 325° F. to about 450° F.

16. The method of claim 1, wherein the step of applying said coating of said elastomeric bonding agent includes applying said coating to one of said opposed surfaces of said ePTFE layer with said bonding agent being disposed within said microporous structure.

17. The method of claim 1, wherein said bonding agent is selected from the group consisting of urethanes, styrene/isobutylene/styrene block copolymers, silicones, and combinations thereof.

18. The method of claim 1, wherein said bonding agent is a polycarbonate urethane.

19. The method of claim 1, wherein said textile layer is knitted textile layer, a woven textile layer, a stretch-knit textile layer, a braided textile layer, and combinations thereof.

20. The method of claim 1, wherein said textile layer and said ePTFE layer are substantially planar.

21. The method of claim 20, wherein said composite device is a vascular patch.

22. The method of claim 1, wherein said elastic silicone barrier member has a thickness of about 0.5 mm to about 1.25 mm.

23. The method of claim 1, wherein said composite textile and ePTFE implantable device has a bond shear strength of at least 5.5 g/mm$^2$ and a variation of said bond shear strength of less than about 2.

24. A method of forming a composite textile and ePTFE implantable device comprising the steps of:

(a) providing an ePTFE layer having opposed surfaces comprising a microporous structure of nodes interconnected by fibrils;

(b) providing a textile layer having opposed surfaces;

(c) providing a self-expanding, radially distensible and metallic stent;

(c) applying a coating of an elastomeric bonding agent to one of said opposed surfaces of said ePTFE layer or said textile layer;

(e) providing a hollow member having an open end and an opposed closed end defining a fluid passageway therebetween and having a wall portion with at least one hole extending therethrough, the hole being in fluid communication with said fluid passageway;

(f) concentrically placing said ePTFE layer, said textile layer and said distensible stent onto said hollow member and over said at least one hole of said hollow member to provide an interior composite layer and an exterior composite layer, wherein said distensible stent is placed between said textile layer and said ePTFE layer, thereby defining a composite assembly, wherein said interior composite layer is one of said ePTFE layer or said textile layer and said exterior composite layer is the other of said ePTFE layer or said textile layer;

(g) placing said hollow member with said composite assembly within a pressure chamber;

(h) applying a positive pressure to said chamber so that the positive pressure within said chamber is higher than a pressure outside of said chamber;

(i) applying a pressure differential so that the pressure within said chamber is greater than a pressure within said fluid passageway of said hollow member; and (j) applying heat to said bonding agent to adhesively bond said textile layer and said ePTFE layer to provide a laminated composite assembly having a bond shear strength of at least 5.5 g/mm2 and a variation of said bond shear strength of less than about 2.

25. The method of claim 24, wherein said textile layer is a hollow tubular textile layer having an inner and outer textile surface and said ePTFE layer is applied to said inner textile surface.

26. The method of claim 24, further including the step of providing a second layer of ePTFE between said stent and said textile layer prior to the step of placing said hollow member within said pressure chamber.

27. A method of forming a composite textile and ePTFE implantable device comprising the steps of:
  providing an ePTFE layer having opposed surfaces comprising a microporous structure of nodes interconnected by fibrils;
  providing a textile layer having opposed surfaces;
  applying a coating of an elastomeric bonding agent to one of said opposed surfaces of said ePTFE layer or said textile layer;
  providing a hollow member having an open end and an opposed closed end defining a fluid passageway therebetween and having a wall portion with at least one hole extending therethrough, the hole being in fluid communication with said fluid passageway;
  providing a pressure controller at the open end of said hollow member;
  concentrically placing said ePTFE layer and said textile layer onto said hollow member and over said at least one hole of said hollow member to provide an interior composite layer and an exterior composite layer, thereby defining a composite assembly, wherein said interior composite layer is one of said ePTFE layer or said textile layer and said exterior composite layer is the other of said ePTFE layer or said textile layer;
  providing an elastic silicone barrier member;
  expanding the elastic silicone member to a diameter greater that that of said hollow tubular member;
  disposing the expanded silicone member over an exterior surface of said exterior composite layer;
  reducing the diameter of the expanded silicone member to cover said aligned ePTFE layer and said aligned textile layer over said hollow member;
  placing said hollow member with said composite assembly within a pressure chamber;
  applying a positive pressure to said chamber so that the positive pressure within said chamber is higher than a pressure outside of said chamber;
  applying a pressure differential so that the pressure within said chamber is greater than a pressure within said fluid passageway of said hollow member;
  controlling said positive pressure and said pressure differential by said pressure controller;
  applying heat to said bonding agent to adhesively bond said textile layer and said ePTFE layer to provide a laminated composite assembly; and
  removing said elastic silicone barrier member from said laminated composite assembly.

28. A method of forming a composite textile and ePTFE implantable device comprising the steps of:
  providing an ePTFE layer having opposed surfaces comprising a microporous structure of nodes interconnected by fibrils;
  providing a textile layer having opposed surfaces;
  applying a coating of an elastomeric bonding agent to one of said opposed surfaces of said ePTFE layer or said textile layer;
  providing a hollow member having an open end and an opposed closed end defining a fluid passageway therebetween and having a wall portion with at least one hole extending therethrough, the hole being in fluid communication with said fluid passageway;
  concentrically placing said ePTFE layer and said textile layer onto said hollow member and over said at least one hole of said hollow member to provide an interior composite layer and an exterior composite layer, thereby defining a composite assembly, wherein said interior composite layer is one of said ePTFE layer or said textile layer and said exterior composite layer is the other of said ePTFE layer or said textile layer;
  providing an elastic silicone barrier member;
  expanding the elastic silicone barrier member to a diameter greater that that of said hollow tubular member;
  disposing the expanded silicone barrier member over an exterior surface of said exterior composite layer;
  reducing the diameter of the expanded silicone barrier member to cover said aligned ePTFE layer and said aligned textile layer over said hollow member;
  placing said hollow member with said composite assembly within a pressure chamber;
  applying a positive pressure to said chamber so that the positive pressure within said chamber is higher than a pressure outside of said chamber;
  applying a pressure differential so that the pressure within said chamber is greater than a pressure within said fluid passageway of said hollow member;
  applying heat to said bonding agent to adhesively bond said textile layer and said ePTFE layer to provide a laminated composite assembly; and
  removing said elastic silicone barrier member from said laminated composite assembly.

29. A method of forming a composite textile and ePTFE implantable device comprising the steps of:
  providing an ePTFE layer having opposed surfaces comprising a microporous structure of nodes interconnected by fibrils;
  providing a textile layer having opposed surfaces;
  applying a coating of an elastomeric bonding agent to one of said opposed surfaces of said ePTFE layer or said textile layer;
  providing a hollow member having an open end and an opposed closed end defining a fluid passageway therebetween and having a wall portion with at least one hole extending therethrough, the hole being in fluid communication with said fluid passageway;
  providing a pressure controller at the open end of said hollow member; concentrically placing said ePTFE layer and said textile layer onto said hollow member and over said at least one hole of said hollow member to provide an interior composite layer
  and an exterior composite layer, thereby defining a composite assembly, wherein said interior composite layer is one of said ePTFE layer or said textile layer and said exterior composite layer is the other of said ePTFE layer or said textile layer;
  providing a thin elastic silicone barrier member having a thickness of about 0.5 mm to about 1.25 mm;
  expanding the thin elastic silicone barrier to a diameter greater that that of said hollow tubular member;
  disposing the expanded thin elastic silicone barrier over an exterior surface of said exterior composite layer;
  reducing the diameter of the expanded thin elastic silicone barrier to cover said aligned ePTFE layer and said aligned textile layer over said hollow member;
  placing said hollow member with said composite assembly within a pressure chamber;

applying a positive pressure to said chamber so that the positive pressure within said chamber is higher than a pressure outside of said chamber;

applying a pressure differential so that the pressure within said chamber is greater than a pressure within said fluid passageway of said hollow member;

applying heat to said bonding agent to adhesively bond said textile layer and said ePTFE layer to provide a laminated composite assembly; and removing said thin elastic silicone barrier member from said laminated composite assembly;

wherein a force exerted by the thin elastic silicone barrier on said aligned ePTFE layer and said aligned textile layer is less than said pressure differential.

30. The method of claim 24, wherein said laminated composite assembly has a bond peel strength of at of at least 32 g/mm and a variation of said bond peel strength of less than about 4.

31. The method of claim 27, wherein said laminated composite assembly has a bond shear strength of at least 5.5 g/mm$^2$ and a variation of said bond shear strength of less than about 2 and a bond peel strength of at of at least 32 g/mm and a variation of said bond peel strength of less than about 4.

32. The method of claim 28, wherein said laminated composite assembly has a bond shear strength of at least 5.5 g/mm$^2$ and a variation of said bond shear strength of less than about 2 and a bond peel strength of at of at least 32 g/mm and a variation of said bond peel strength of less than about 4.

33. The method of claim 29, wherein said laminated composite assembly has a bond shear strength of at least 5.5 g/mm$^2$ and a variation of said bond shear strength of less than about 2 and a bond peel strength of at of at least 32 g/mm and a variation of said bond peel strength of less than about 4.

* * * * *